(12) United States Patent
Childers et al.

(10) Patent No.: US 7,179,943 B2
(45) Date of Patent: Feb. 20, 2007

(54) BICYCLIC DERIVATIVES THAT MODULATE VOLTAGE-GATED POTASSIUM CHANNELS AND METHODS OF USE THEREOF

(75) Inventors: Wayne E. Childers, New Hope, PA (US); Jerome C. Wu, Princeton, NJ (US); Callain Y. Kim, Collegeville, PA (US); Edward J. Podlesny, New Tripoli, PA (US)

(73) Assignee: Wyeth, Madison, NJ (US)

( * ) Notice: Subject to any disclaimer, the term of this patent is extended or adjusted under 35 U.S.C. 154(b) by 38 days.

(21) Appl. No.: 11/151,624

(22) Filed: Jun. 13, 2005

(65) Prior Publication Data

US 2006/0004108 A1    Jan. 5, 2006

Related U.S. Application Data

(60) Provisional application No. 60/579,203, filed on Jun. 14, 2004.

(51) Int. Cl.
*C07C 233/58* (2006.01)
*C07C 45/27* (2006.01)
*A61K 31/165* (2006.01)

(52) U.S. Cl. .............. 564/188; 514/613; 514/623; 568/338; 568/361; 568/374

(58) Field of Classification Search .............. 564/188; 514/613, 623; 568/338, 361, 374
See application file for complete search history.

(56) References Cited

U.S. PATENT DOCUMENTS

| | | | | |
|---|---|---|---|---|
| 3,746,765 | A | * | 7/1973 | Ruschig et al. ............ 564/74 |
| 4,134,987 | A | | 1/1979 | Huppatz |
| 4,324,912 | A | * | 4/1982 | Klemarczyk et al. ...... 564/188 |
| 2003/0024001 | A1 | | 1/2003 | Wyeth |

FOREIGN PATENT DOCUMENTS

| | | |
|---|---|---|
| DE | 27 01 091 A1 | 7/1977 |
| DE | 44 17 474 A1 | 11/1995 |
| JP | 56008327 A2 | 1/1981 |
| JP | 63010781 A2 | 7/1988 |
| JP | 02157266 A2 | 6/1990 |

OTHER PUBLICATIONS

C. Oliver Kappe et al., J. Org. Chem., 58, 3361-3367 (1993).
K.J. Angelides et al., The Journal of Biological Chemistry, 258(19), 11948-11957 (1983).
G. Shi et al., Neuron, 16, 843-852 (1996).
J. Xu et al., Trends Cardiovascular Medicine, 8(5), 229-234 (1998).
S. Smart et al., Neuron, 20, 809-819 (1998).
S.M. Zuberi et al., Brain, 122, 817-825 (1999).
V.S. Velezheva et al., Zhurnal Organicheskoi Khimii, 14(8), 1712-1723 (1978).
J. H. Nelson et al., Synth. React. Inorg. Met.-Org. Chem., 9(5), 435-444 (1979).
D. Browne et al., Nature Genetics, 8, 136--140 (1994).
J. Rettig et al., Nature, 369, 289-294 (1994).
E. Isacoff et al., Nature, 353, 86-90 (1991).
J. Rho et al., Dev. Neurosci., 21, 320-327 (1999).
O. Pongs et al., Annals New York Academy of Sciences, 868, 344--355 (1999).
K. Uehara et al., Bullentin of the Chemical Society of Japan, 49(5), 1447-1448 (1976).
S. Yamaguchi et al., Epilepsy Res., 11, 9-16 (1992).
C. Miller, Science, 252, 1092-1096 (1991).
W. Zagotta et al., Science, 250-568-571 (1990).
J. Butterworth et al., Anesthesiology, 72, 711-734 (1990).
E. Sledziewska et al., Roczneki Chemn Ann. Soc. Chim. Polonorum, 49, 733-742 (1975).
H. Kolb, Rev. Physiol. Biochem. Pharmacol., 115, 51-91 (1990).
A. Davies et al., J. Chem. Soc., 1479-1483 (1968).
B. Barsoum et al., Indian Journal of Chemistry, 25A, 694-695 (1986).
J. Nelson et al., Fundam. Res. Homogeneous Catal. 3, 921-939 (1979).
M. Kamal et al., Dirasat. [Ser.]: Nat. Sci. (Univ. Jordan), 7, 33-40 (1980).
P. Schwartzkroin et al., Brain Research, 185, 169-181 (1980).
N. Singh et al., Nat. Genet., 18, 25-29 (1998).
K. Rhodes et al., The Journal of Neuroscience, 17(21), 8246-8258 (1997).
G. Gandolfo et al., Brain Research, 495, 189-192 (1989).
J. Bidard et al., Brain Research, 495, 45-57 (1989).

(Continued)

*Primary Examiner*—Shailendra Kumar
(74) *Attorney, Agent, or Firm*—Kimberly R. Hild

(57) ABSTRACT

Bicyclic amide derivatives of formula (I) or tautomers or pharmaceutically acceptable salts thereof or both are provided:

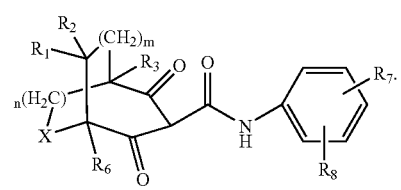

Also provided are processes for preparing the bicyclic amide derivatives as well as pharmaceutical compositions containing the same and therapeutic uses. The bicyclic amide derivatives are useful for treating a variety of conditions associated with the abnormal modulation of one or more Kv1.1 voltage-gated potassium channels.

27 Claims, No Drawings

OTHER PUBLICATIONS

J. Kenney et al., J.C.S. Chem. Comm., 690-691 (1973).
M. Madeja et al., European Journal of Neuroscience, 9, 39-395 (1997).
D. Prince, Ann. Rev. Neurosci., 1, 395-415 (1978).
M. Tsaur et al., Neuron, 8, 1055-1067 (1992).
S. Heinemann et al., Journal of Physiology, 493(3), 625-633 (1996).
SM Zuberi et al., Epilepsia, 38(3), 104 (1997).
C. Biervert et al., Science, 279, 403-406 (1998).
C. Charlier et al., Nature Genetics, 18, 53-55 (1998).
S. Zini et al., Neuroscience Letters, 153, 202-205 (1993).
L. Hevesi et al., Bulletin De La Societe Chimique De France, 11, 3971-3975 (1970).
L. Hevesi et al., Bulletin De La Societe Chimique De France, 11, 4066-4072 (1971).
G. Kollenz et al., Z. Naturforsch, 31b, 1511-1514 (1976).
M.V. Rubtsov, Khim. Geterotsikl, Socdin, 10, 1432-1435 (1976).
E. Ziegler et al., Synthesis, 11, 679-680 (1973).
A. Kettrup et al., Z. Anal. Chem. 269, 118-121 (1974).
Macias et al., Zhurnal Organicheskoi Khimii, 18(7), 1386-1390 (1982); translation attached Journal of Organic Chemistry of the USSR, 18, 1205-1208 (1982).
M. Ocana et al., European Journal of Pharmacology, 500, 203-219 (2004).

* cited by examiner

BICYCLIC DERIVATIVES THAT MODULATE VOLTAGE-GATED POTASSIUM CHANNELS AND METHODS OF USE THEREOF

CROSS-REFERENCE TO RELATED APPLICATIONS

This application claims the benefit under 35 U.S.C. §119 (e) to U.S. provisional application 60/579,203, filed Jun. 14, 2004, which is hereby incorporated by reference in its entirety.

BACKGROUND OF THE INVENTION

The present invention relates to bicyclic amide derivatives, to processes for their preparation, and to their use in therapeutic treatments.

Ion channels are transmembrane proteins that regulate the passage of various ions through the membrane. Ion channels are physiologically important, playing essential roles in regulating intracellular levels of various ions and in generating or modulating action potentials in nerve and muscle cells. Passage of ions through ion channels is characterized by selective filtering and by a gating-type mechanism which produces a rapid increase in permeability (Angelides, K. J., et al., *J. Biol. Chem.*, 1981, 258, 11858). Ion channels may be either voltage-gated, implying that current is gated (or regulated) by membrane potential (voltage), or chemically-gated, implying that current is gated primarily by binding of a chemical agent rather than by the membrane potential (Butterworth, J. F., et al., *Anesthesiology*, 1980, 72, 711). An important characteristic of certain voltage-gated ion channels is inactivation. Soon after opening, these channels close via various mechanisms, forming an inactive channel complex that will not return to its active state until the membrane is repolarized (Miller, C., *Science*, 1991, 252, 1092).

The ion-conduction pore of these channels is composed of heterotetramers of different, but structurally-related, α-subunits. Each α-subunit consists of an approximately 600-amino-acid polypeptide which possesses six membrane-spanning α-helices (Kolb, 1990; Shi, G., et al., *Neuron*, 1996, 16, 843). The α-subunits of mammalian voltage-gated potassium channels are currently divided into four related gene-families, based on homology with the corresponding gene families originally derived from work with *Drosophila melanogaster*. These four groups are the Kv1 (Kv1.1-1.8, the so called Shaker family), Kv2 (Kv2.1-2.2, the Shab family), Kv3 (Kv3.1-3.4, the Shaw family) and Kv4 (Kv4.1-4.1, the Shal family) gene subfamilies (for a review, see Chandy, K. G. and Gutman, G. A., in *Handbook of Receptors and Channels: Ligand and Volgate-Gated Ion Channels*, CRC Press, pages 1 to 71, 1995 and references cited within.

In some cases, each α-subunit is closely associated with a β-subunit which does not participate in ion conductance directly but can regulate the activity of the channel (for reviews, see: Xu, J. and Li, M., *Trends Cardiovasc. Med.*, 1998, 8, 229; Pongs, O., et al., *Ann. N.Y. Acad. Sci.*, 1999, 868, 344). The known β-subunits have been assigned to three classes, Kvβ1-3, and several splice variants of Kvβ1 have also been described. One well-documented activity of the Kvβ1 subunit is to confer rapid inactivation on the current-conducting α-subunit, which normally displays slow inactivation in the absence of the β-subunit (Rettig, J., et al., *Nature*, 1994, 369, 289). As in the *Drosophila*-derived Shaker family, the inactivation conferred by mammalian Kvβ1 involves the N-type "ball-and-chain" mechanism (Zagotta, W. N., et al., *Science*, 1990, 250, 568; Isacoff, E. Y., et al., *Nature*, 1991, 353, 86). Thus, in this role Kvβ1 acts as a switch, shutting off the voltage-gated potassium channel once it has performed its function of repolarizing the membrane.

Voltage-gated potassium ($K_V$) channels participate in several cellular processes. In excitable tissues, these ion channels play an essential role in establishing the resting membrane potential and in modulating the frequency and duration of the action potential (Hille, B., *Ionic Channels of Excitable Membranes*, Sunderland, Mass., 1992). In nonexcitable cells, they are involved in cell volume regulation, hormone secretion, oxygen sensing and cell proliferation (Kolb., H. A., *Rev. Physiol. Biochem. Pharmacol.*, 1990, 115, 51). Thus, Kv channels are key regulators of neuronal excitability and their dysfunction is believed to be associated with a variety of abnormal conditions or diseases.

For example, implications for a role of Kv1.1 in epilepsy come from varied sources (for a review, see Rho, J. M., *Dev. Neurosci.*, 1999, 21, 320). Kv1.1 genes are richly expressed in brain regions which are susceptible to epileptic seizure, such as hippocampus and neocortex. Kv1.1 potassium channels have been shown to play a role in epilepsy based on recent cloning experiments where deletion of the Kv1.1 potassium channel in mice causes epilepsy (Smart, S. L., et al., *Neuron*, 1998, 20, 809). In vitro, tissue manipulations using material from these animals which only marginally increase excitability in normal tissue (e.g., raising extracellular potassium or treatment with the $GABA_A$ antagonist bicuculine) result in synchronous burst discharges and long-lasting depolarizations in hippocampal CA3 pyramidal neurons. Furthermore, mutations in human genes thought to correspond to Kv1.1 result in hyperexcitable phenotypes, including cases of episodic ataxia and myokymia (Browne, D. L., et al., *Nat. Genet.*, 1994, 8, 136) as well as benign neonatal convulsions, an autosomal dominant form of early-onset epilepsy (Biervert, C., et al., *Science*, 1998, 279, 403; Charlier, C., et al., *Nat. Genet.*, 1998, 18, 53; Singh, N. A., et al., *Nat. Genet.*, 1998, 18, 25). Additionally, reports of epilepsy in family members affected by the Kv1.1 mutation and diagnosed with episodic ataxia and myokymia have appeared (Zuberi, S. M., et al., *Epilepsia*, 1997, 38 (supp. 3), 104; Zuberi, S. M., et al., *Brain*, 1999, 122, 817), correlating the Kv1.1 gene mutation with epilepsy.

Thus, the available evidence suggests that a decrease in Kv1.1 function may act as a mitigating factor in neuronal hyperexcitable disease states, such as epilepsy. Other disease states or conditions affected by neuronal hyperexcitability include for example episodic ataxia, myokymia, neonatal-convulsions, cerebral ischemia, cerebral palsy, stroke, traumatic brain injury, traumatic spinal cord injury, asphyxia, anoxia or prolonged cardiac surgery.

It has also been shown that potassium ion channel openers also play a role in the release and/or regulation of glutamate in mammals (Zini, S. et al., Neuroscience Letters, 1993, 153:202–205). Thus, it is believed compounds that inhibit the inactivation of Kv1.1 will be useful for treating conditions associated with the abnormal release of glutamate including for example hypoglycemia or diseases associated with glutamate release such as Parkinson's disease, Huntingdon's disease, Alzheimer's disease, amyotrophic lateral sclerosis, or AIDS related dementia or combinations thereof.

Thus it would be desirable to find agents that activate Kv1.1 currents or inhibit the inactivation of Kv1.1 currents in mammals. Moreover, as it has been shown that Kv1.1 α-subunits associate and co-localize with Kvβ1 in seizure-sensitive brain regions (Rhodes, K. J., et al., *J. Neurosci.*,

SUMMARY OF THE INVENTION

The present invention relates to bicyclic phenyl amide derivatives, pharmaceutical compositions containing the bicyclic amide derivatives, and methods of use thereof. The bicyclic amide derivatives preferably activate or inhibit the inactivation of Kv1.1 voltage gated potassium channels.

In certain embodiments, the invention relates to compounds of formula (I):

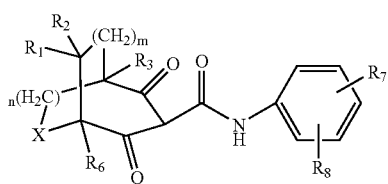

or a tautomer thereof, or a pharmaceutically acceptable salt thereof or both, where:

X is a bond or $CR_4R_5$;

$R_1$, $R_2$, $R_4$, and $R_5$ are, independently, hydrogen or a $C_1$ to $C_6$ alkyl;

$R_3$ and $R_8$ are, independently hydrogen or a $C_1$ to $C_6$ alkyl;

$R_7$ and $R_8$ are, independently, hydrogen, a halogen atom, a hydroxyl group, a $C_1$ to $C_6$ alkyl, a $C_1$ to $C_6$ alkoxy, a $C_1$ to $C_4$ perhalogenated alkyl, a $C_1$ to $C_4$ perhalogenated alkoxy, a $C_2$ to $C_7$ alkenyl, CN, $NO_2$, $CO_2R_9$, $COR_9$, alkanesulfonyl, or $NR_9R_{10}$;

m and n are, independently, 0 or 1; and $R_9$ and $R_{10}$ are, independently, hydrogen or a $C_1$ to $C_6$ alkyl.

In certain other embodiments, the invention relates to methods for treating one or more conditions in a mammal associated with the abnormal inactivation of one or more Kv1.1 voltage-gated potassium channels. The methods include administering to a mammal a therapeutically effective amount of at least one compound of formula (I), or a tautomer thereof or a pharmaceutically acceptable salt thereof or both. Conditions that may be treated in accordance with the methods of the present invention include conditions related to neuronal hyperexcitability such as convulsions, epilepsy, episodic ataxia, myokymia, neonatal convulsions, cerebral ischemia, cerebral palsy, stroke, traumatic brain injury, traumatic spinal cord injury, asphyxia, anoxia or prolonged cardiac surgery; conditions related to the release of glutamate such as pain, Alzheimer's disease, Parkinson's disease, hypoglycemia, Huntingdon's disease, amyotrophic lateral sclerosis, or AIDS related dementia; and anxiety disorders.

In still other embodiments, the invention relates to compositions comprising at least one compound of formula (I) or a tautomer thereof or a pharmaceutically acceptable salt thereof, or both; and one or more pharmaceutically acceptable carriers.

In yet other embodiments, processes are provided for preparing compounds of formulas (I) and (III).

DETAILED DESCRIPTION OF ILLUSTRATIVE EMBODIMENTS

The present invention relates to bicyclic phenyl amide derivatives that preferably inhibit the inactivation of the Kv1.1 voltage-gated potassium channels, processes for preparing such compounds, including intermediates, pharmaceutical compositions containing such compounds, and therapeutic methods for using such compounds. In some embodiments, compounds of the present invention, when administered to a mammal in need thereof, preferably facilitate the activation (such as increasing activation) or inhibit the inactivation of one or more Kv1.1 voltage-gated potassium channels. In other embodiments, the compounds of the present invention interact with one or more Kvβ1 subunits to inhibit inactivation.

As used herein, unless otherwise indicated, "alkyl" refers to a $C_1$ to $C_6$ aliphatic hydrocarbon chain and includes straight or branched chains such as methyl, ethyl, n-propyl, isopropyl, n-butyl, isobutyl, sec-butyl, t-butyl, n-pentyl, isopentyl, neo-pentyl, n-hexyl, isohexyl. Preferably, alkyl groups contain 1 to 4 carbon atoms. "Alkenyl" refers to a $C_2$ to $C_7$ aliphatic hydrocarbon chain including straight or branched chains that contains at least one double bond and more preferably 1 to 3 double bonds. Examples of alkenyl groups include vinyl, prop-1-enyl, allyl, methallyl, but-1-enyl, but-2-enyl, but-3-enyl, or 3,3-dimethylbut-1-enyl.

The term "perhalogenated alkyl," as used herein, refers to a straight or branched aliphatic hydrocarbon chain of 1 to 4 carbon atoms and preferably 1 to 3 carbon atoms, in which all hydrogens are replaced with halogen atoms.

The term "alkoxy," as used herein, refers to the group R—O— where R is an alkyl group of 1 to 6 carbon atoms.

The term "perhalogenated alkoxy," as used herein, refers to the group R—O where R is a perhalogenated alkyl group of 1 to 4 carbon atoms.

The term "aryl" refers to an aromatic 5- to 7-membered monocarbocyclic ring such as phenyl.

The term "alkanesulfonyl" refers to the group R—S(O)$_2$— where R is an alkyl group as previously described.

Halogen means fluorine, chlorine, bromine or iodine.

Unless stated otherwise, any moiety containing an alkyl, alkenyl, or aryl group may be unsubstituted or optionally substituted with one to three substituents as defined hereinafter. For example, alkyl moieties may be halogenated, such as mono- or difluoromethyl or mono- or difluoromethoxy.

The term "substituted" as used herein refers to a moiety, such as an alkyl, alkenyl, or aryl group having from 1 to 3 substituents independently selected from a halogen atom, CN, $NO_2$, hydroxyl group, a $C_1$–$C_6$ alkyl group, a $C_1$–$C_6$ alkoxy group, a $C_1$–$C_4$ perhalogenated alkyl group or $C_1$–$C_4$ perhalogenated alkoxy group. Preferred substituents are halogen atoms, CN, $NO_2$, hydroxyl group, $C_1$–$C_6$ alkyl groups, or $C_1$–$C_6$ alkoxy groups.

"Condition associated with the abnormal inactivation of one or more Kv1.1 voltage-gated potassium channels" refers to any abnormal functioning of a mammal or any disease present in a mammal that can at least be partially attributed to abnormal inactivation or abnormally decreased activation of one or more Kv1.1 voltage-gated potassium channels. Examples of conditions that are associated with the inactivation of Kv1.1 voltage-gated potassium channel are described in further detail hereinafter.

"Treating" means partially or completely alleviating, inhibiting, preventing and/or ameliorating the condition. For example, "treating" as used herein includes partially or completely alleviating, inhibiting, preventing and/or ameliorating epilepsy.

"Mammal" refers to any warm blooded species, such as a human. administering a prodrug derivative or analog of the compound to the mammal, which will form an equivalent amount of the active compound or substance within the mammal's body.

The terms "effective amount" and "therapeutically effective amount," as used herein, refer to the amount of a compound of formula (I) that, when administered to a mammal, is effective to at least partially alleviating, inhibiting, preventing and/or ameliorating a condition from which the mammal is suspected to suffer. Such conditions include, but are not limited to, epilepsy, stroke, cerebral ischemia, cerebral palsy, hypoglycemia, Alzheimer's disease, Huntington's disease, asphyxia, anoxia, neuropathic pain, spinal cord trauma, or traumatic brain injury.

"Kv1.1 voltage-gated potassium channel" refers to a voltage-gated potassium channel containing at least one Kv1.1 α subunit.

"Kv1.1/Kvβ1" refers to a voltage gated potassium channel that contains at least one Kv1.1 α subunit and that is associated with at least one Kvβ1 subunit.

"Inactivation" refers to the closing of the potassium channel by any mechanism such as by N-type inactivation. "Activation" refers to the potassium channel being open so that current can flow through. Types of inactivation are discussed for example in Hille, B., *Ionic Channels of Excitable Membranes*, Sunderland, Mass., 1992, which is hereby incorporated by reference in its entirety.

"Pharmaceutically acceptable" refers to a substance that is acceptable for use in pharmaceutical applications from a toxicological perspective and does not adversely interact with the active ingredient.

In certain embodiments, the invention relates to compounds of formula (I):

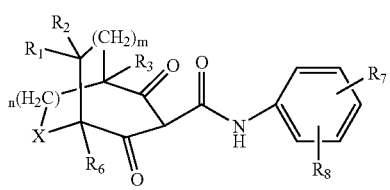

(I)

or a tautomer thereof, or a pharmaceutically acceptable salt thereof or both, where:

X is a bond or $CR_4R_5$;

$R_1$, $R_2$, $R_4$, and $R_5$ are, independently, hydrogen or a $C_1$ to $C_6$ alkyl;

$R_3$ and $R_6$ are, independently hydrogen or a $C_1$ to $C_6$ alkyl;

$R_7$ and $R_8$ are, independently, hydrogen, a halogen atom, a hydroxyl group, a $C_1$ to $C_6$ alkyl, a $C_1$ to $C_6$ alkoxy, a $C_1$ to $C_4$ perhalogenated alkyl, a $C_1$ to $C_4$ perhalogenated alkoxy, a $C_2$ to $C_7$ alkenyl, CN, $NO_2$, $CO_2R_9$, $COR_9$, alkanesulfonyl, or $NR_9R_{10}$;

m and n are, independently, 0 or 1; and $R_9$ and $R_{10}$ are, independently, hydrogen or a $C_1$ to $C_6$ alkyl.

The phrases n=0 and m=0 are taken to mean that a single bond exists between the two carbons of the ring spanned by the descriptor —(CH$_2$)$_n$— or —(CH$_2$)$_m$— respectively. The phrase "X is a bond" is taken to mean that a single bond exists between the two carbons of the ring spanned by —X—.

Compounds useful in the present invention also include all tautomers of formula (I), all pharmaceutically acceptable salts of formula (I), or both (i.e., pharmaceutically acceptable salts of tautomers of formula (I)). Examples of tautomers of formula (I) include:

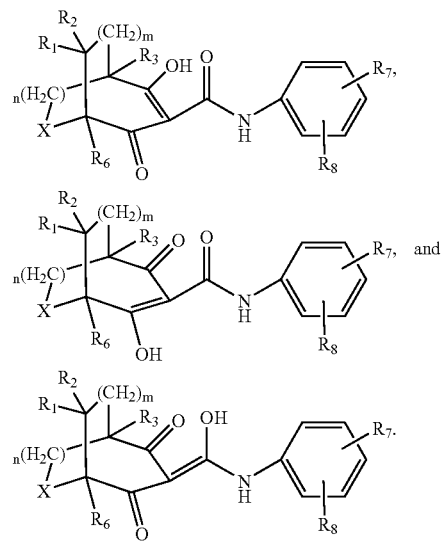

By "pharmaceutically acceptable salt", it is meant any compound formed by the addition of a pharmaceutically acceptable inorganic or organic base and a compound of formula (I) to form the corresponding salt, or if a basic substituent (e.g., an amino group) is present on the compound of formula (I), any compound formed by the addition of a pharmaceutically acceptable organic or inorganic acid and a compound of formula (I). Examples of pharmaceutically acceptable inorganic or organic bases include alkali metal or alkaline earth metal hydroxides, ammonia, ammonium hydroxide, or basic amines. Examples of organic and inorganic acids include for example, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids. Examples of pharmaceutically acceptable salts useful in this invention include alkali metal (e.g., sodium, potassium, lithium) or alkaline earth metal (e.g., calcium, magnesium) salts of the compounds of formula (I). Examples of salts of formula I formed by the reaction of ammonia, ammonium hydroxide, or a basic amine include the corresponding ammonium; mono-, di-, or trimethylammonium; mono-, di, or triethylammonium; mono-, di-, or tripropylammonium (iso or normal); ethyldimethylammonium; benzyldimethylammonium; cyclohexylammonium; benzylammonium; dibenzylammonium; piperidinium; morpholinium; pyrrolidinium; piperazinium; 1-methylpiperidinium; 1-isopropylpyrrolidinium; 1,4-dimethylpiperazinium; 1-n-butylpiperidinium; 2-methylpiperidinium; 1-ethyl-2-methylpiperidinium; mono-, di-, or triethanolammonium; tris-(hydroxymethyl)methylammonium; or phenylmonoethanolammonium salt.

One skilled in the art will also recognize that the compounds useful in the present invention may contain at least one asymmetric center. While shown without respect to stereochemistry in Formula (I), the compounds useful in the present invention include all optical isomers and diastereoisomers, including all individual isomers, enantiomers, diasteromers or mixtures thereof. In preferred embodiments, the invention relates to all of the stereoisomers of the bicyclic amide derivatives, as well as to mixtures of the stereoisomers. Throughout this application, the name of the product, where the absolute configuration of an asymmetric center is not indicated, is intended to embrace the individual stereoisomers as well as mixtures of stereoisomers. When it is necessary to distinguish the enantiomers from one another, "R" and "S" designations are used. Furthermore, throughout this application, the designations R* and S* are used to indicate relative stereochemistry, employing the Chemical Abstracts convention which automatically assigns R* to the lowest numbered asymmetric center. The compounds useful in the present invention may be prepared as mixtures of the isomers (e.g., racemic) and can be used as such, or may be resolved into the individual isomers.

Where an enantiomer is preferred, it may, in some embodiments be provided substantially free of the corresponding enantiomer. Thus, an enantiomer substantially free of the corresponding enantiomer refers to a compound which is isolated or separated via separation techniques or prepared free of the corresponding enantiomer. "Substantially free," as used herein, means that the compound is made up of a significantly greater proportion of one enantiomer. In preferred embodiments the compound is made up of at least about 90% by weight of a preferred enantiomer. In other embodiments of the invention, the compound is made up of at least about 99% by weight of a preferred enantiomer. Preferred enantiomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

In certain embodiments of the invention, $R_1$, $R_2$, $R_4$, and $R_5$ are, independently, H or methyl. In other embodiments, $R_1$ and $R_2$ are each methyl, and $R_4$ and $R_5$ are each H. In further embodiments, $R_1$ and $R_2$ are each H, and $R_4$ and $R_5$ are each methyl. In still further embodiments, $R_1$, $R_2$, $R_4$, and $R_5$ are each H.

In yet other embodiments of the invention, $R_3$ and $R_6$ are, independently, H or methyl.

In certain other embodiments of the invention, m is 0 and n is 1. In other embodiments, m and n are each 0. In other embodiments, m and n are each 1.

In other embodiments of the invention, X is $CR_4R_5$. In still other embodiments, X is a bond, n is 0 and m is 0 to form a bicyclohexane ring such as 6,6-dimethyl-bicyclo [3.1.0]hexane-2,4-dione.

In further embodiments of the invention, $R_7$ and $R_8$ are, independently, H, $C_1$ to $C_4$ alkyl, halogen, nitro, $C_1$ to $C_6$ dialkylamino, or $C_1$ to $C_4$ perhalogenated alkyl. In other embodiments, $R_7$ and $R_8$ are, independently, H, methyl, chlorine, fluorine, nitro, perfluoromethyl, or dimethylamino. In some emdoments, positions on the phenyl ring for non-hydrogen $R_7$ and $R_8$ substituents include: the 3- or 4-position where one of $R_7$ or $R_8$ is not hydrogen, and the 3-, 4- or 3-, 5-positions where both $R_7$ and $R_8$ are not hydrogen.

In still further embodiments of the invention, X is $CR_4R_5$; $R_1$, $R_2$, $R_4$, and $R_5$ are, independently, H or methyl; $R_3$ and $R_6$ are, independently, H or methyl; m is 0 and n is 1; and $R_7$ and $R_8$ are, independently, H, alkyl, halogen, nitro, $C_1$ to $C_6$ dialkylamino, or $C_1$ to $C_4$ perhalogenated alkyl. In still further embodiments of the invention, $R_1$, $R_2$, $R_4$, and $R_5$ are, independently, H or methyl; $R_3$ and $R_6$ are, independently, H or methyl; m and n are each 0; and $R_7$ and $R_8$ are, independently, H, alkyl, halogen, nitro, $C_1$ to $C_6$ dialkylamino, or $C_1$ to $C_4$ perhalogenated alkyl.

In certain other embodiments of the invention, X is $CR_4R_5$; $R_1$ and $R_2$ are each methyl, and $R_4$ and $R_5$ are each H; $R_3$ and $R_6$ are, independently, H or methyl; m is 0 and n is 1; and $R_7$ and $R_8$ are, independently, H, alkyl, halogen, nitro, $C_1$ to $C_6$ dialkylamino, or $C_1$ to $C_4$ perhalogenated alkyl. In other embodiments, X is $CR_4R_5$; m is 0 and n is 1; $R_1$ through $R_6$ are H; and $R_7$ and $R_8$ are, independently, H, alkyl, halogen, nitro, $C_1$ to $C_6$ dialkylamino, or $C_1$ to $C_4$ perhalogenated alkyl. In yet other embodiments of the invention, X is $CR_4R_5$; $R_1$ and $R_2$ are each H, and $R_4$ and $R_5$ are each methyl; $R_3$ and $R_6$ are, independently, H or methyl; m and n are each 0; and $R_7$ and $R_8$ are, independently, H, alkyl, halogen, nitro, $C_1$ to $C_6$ dialkylamino, or $C_1$ to $C_4$ perhalogenated alkyl. In still other embodiments, X is $CR_4R_5$; m and n are each 1; $R_1$ through $R_6$ are H; and $R_7$ and $R_8$ are, independently, H, alkyl, halogen, nitro, $C_1$ to $C_6$ dialkylamino, or $C_1$ to $C_4$ perhalogenated alkyl.

In still other embodiments, X is $CR_4R_5$; $R_1$, $R_2$, $R_4$, and $R_5$ are each H; $R_3$ and $R_6$ are, independently, H or methyl; m is 0 and n is 1; and $R_7$ and $R_8$ are, independently, H, alkyl, halogen, nitro, $C_1$ to $C_6$ dialkylamino, or $C_1$ to $C_4$ perhalogenated alkyl. In other embodiments, X is $CR_4R_5$; $R_1$, $R_2$, $R_4$, and $R_5$ are each H or methyl; $R_3$ and $R_6$ are each H; m and n are each 0; and $R_7$ and $R_8$ are, independently, H, alkyl, halogen, nitro, $C_1$ to $C_6$ dialkylamino, or $C_1$ to $C_4$ perhalogenated alkyl.

In yet further embodiments of the invention, the compounds of formula (I) include:

N-[3,5-bis(trifluoromethyl)phenyl]-1,8,8-trimethyl-2,4-dioxobicyclo[3.2.1]octane-3-carboxamide;

N-[3-(trifluoromethyl)phenyl]-1,8,8-trimethyl-2,4-dioxobicyclo[3.2.1]octane-3-carboxamide;

N-(3,5-dichlorophenyl)-1,8,8-trimethyl-2,4-dioxobicyclo[3.2.1]octane-3-carboxamide;

N-(3,4-dichlorophenyl)-1,8,8-trimethyl-2,4-dioxobicyclo[3.2.1]octane-3-carboxamide;

N-(3-nitrophenyl)-1,8,8-trimethyl-2,4-dioxobicyclo[3.2.1]octane-3-carboxamide;

N-(4-nitrophenyl)-1,8,8-trimethyl-2,4-dioxobicyclo[3.2.1]octane-3-carboxamide;

N-[4-chloro-3-(trifluoromethyl)phenyl]-1,8,8-trimethyl-2,4-dioxobicyclo[3.2.1]octane-3-carboxam N-[4-(trifluoromethyl)phenyl]-1,8,8-trimethyl-2,4-dioxobicyclo[3.2.1]octane-3-carboxamide;

N-[4-(dimethylamino)phenyl]-1,8,8-trimethyl-2,4-dioxobicyclo[3.2.1]octane-3-carboxamide;

N-[3-chloro-4-fluorophenyl]-1,8,8-trimethyl-2,4-dioxobicyclo[3.2.1]octane-3-carboxamide;

N-[4-methylphenyl]-1,8,8-trimethyl-2,4-dioxobicyclo[3.2.1]octane-3-carboxamide;

N-[4-fluoro-3-(trifluoromethyl)phenyl]-1,8,8-trimethyl-2,4-dioxobicyclo[3.2.1]octane-3-carboxam N-[4-chlorophenyl]-1,8,8-trimethyl-2,4-dioxobicyclo[3.2.1]octane-3-carboxamide;

N-[3-(trifluoromethyl)phenyl]-2,4-dioxobicyclo[3.2.1]octane-3-carboxamide;

N-[3,5-bis(trifluoromethyl)phenyl]-2,4-dioxobicyclo[3.2.1]octane-3-carboxamide;

N-([3,4-dichlorophenyl)-2,4-dioxobicyclo[3.2.1]octane-3-carboxamide;
N-[4-chloro-3-(trifluoromethyl)phenyl]-2,4-dioxobicyclo[3.2.1]octane-3-carboxamide;
N-[4-(trifluoromethyl)phenyl]-2,4-dioxobicyclo[3.2.1]octane-3-carboxamide;
N-[4-fluoro-3-(trifluoromethyl)phenyl]-2,4-dioxobicyclo[3.2.1]octane-3-carboxamide;
6,6-Dimethyl-2,4-dioxo-N-[4-(trifluoromethyl)phenyl]bicyclo[3.1.1]heptane-3-carboxamide;
6,6-Dimethyl-2,4-dioxo-N-[3-(trifluoromethyl)phenyl]bicyclo[3.1.1]heptane-3-carboxamide;
6,6-Dimethyl-2,4-dioxo-N-(3-chloro-4-fluorophenyl)bicyclo[3.1.1]heptane-3-carboxamide;
6,6-Dimethyl-2,4-dioxo-N-[4-fluoro-3-(trifluoromethyl)phenyl]bicyclo[3.1.1]heptane-3-carboxamid
6,6-Dimethyl-2,4-dioxo-N-(3,4-dichlorophenyl)bicyclo[3.1.1]heptane-3-carboxamide;
6,6-Dimethyl-2,4-dioxo-N-(3,5-dichlorophenyl)bicyclo[3.1.1]heptane-3-carboxamide;
6,6-Dimethyl-2,4-dioxo-N-(4-fluorophenyl)bicyclo[3.1.1]heptane-3-carboxamide;
6,6-Dimethyl-2,4-dioxo-N-(3-chlorophenyl)bicyclo[3.1.1]heptane-3-carboxamide;
6,6-Dimethyl-2,4-dioxo-N-(4-chlorophenyl)bicyclo[3.1.1]heptane-3-carboxamide; or
N-[3,5-bis(trifluoromethyl)phenyl]-2,4-dioxobicyclo[3.2.2]nonane-3-carboxamide; or
tautomers thereof, pharmaceutically acceptable salts thereof, or both.

Examples of enantiomers include:
(1S)-N-[3,5-bis(trifluoromethyl)phenyl]-1,8,8-trimethyl-2,4-dioxobicyclo[3.2.1]octane-3-carboxamide;
(1S)-N-[3-(trifluoromethyl)phenyl]-1,8,8-trimethyl-2,4-dioxobicyclo[3.2.1]octane-3-carboxamide;
(1S)-N-(3,5-dichlorophenyl)-1,8,8-trimethyl-2,4-dioxobicyclo[3.2.1]octane-3-carboxamide;
(1S)-N-(3,4-dichlorophenyl)-1,8,8-trimethyl-2,4-dioxobicyclo[3.2.1]octane-3-carboxamide;
(1S)-N-(3-nitrophenyl)-1,8,8-trimethyl-2,4-dioxobicyclo[3.2.1]octane-3-carboxamide;
(1S)-N-(4-nitrophenyl)-1,8,8-trimethyl-2,4-dioxobicyclo[3.2.1]octane-3-carboxamide;
(1S)-N-[4-chloro-3-(trifluoromethyl)phenyl]-1,8,8-trimethyl-2,4-dioxobicyclo[3.2.1]octane-3-carboxamide;
(1S)-N-[4-fluoro-3-(trifluoromethyl)phenyl]-1,8,8-trimethyl-2,4-dioxobicyclo[3.2.1]octane-3-carboxamide;
(1S)-N-[4-(trifluoromethyl)phenyl]-1,8,8-trimethyl-2,4-dioxobicyclo[3.2.1]octane-3-carboxamide;
(1S)-N-[4-(dimethylamino)phenyl]-1,8,8-trimethyl-2,4-dioxobicyclo[3.2.1]octane-3-carboxamide;
(1S)-N-[3-chloro-4-fluorophenyl]-1,8,8-trimethyl-2,4-dioxobicyclo[3.2.1]octane-3-carboxamide;
(1S)-N-[4-chlorophenyl]-1,8,8-trimethyl-2,4-dioxobicyclo[3.2.1]octane-3-carboxamide;
(1S)-N-[4-methylphenyl]-1,8,8-trimethyl-2,4-dioxobicyclo[3.2.1]octane-3-carboxamide;
(1R)-N-[3,5-bis(trifluoromethyl)phenyl]-1,8,8-trimethyl-2,4-dioxobicyclo[3.2.1]octane-3-carboxamide;
(1R)-N-(3,5-dichlorophenyl)-1,8,8-trimethyl-2,4-dioxobicyclo[3.2.1]octane-3-carboxamide;
(1R)-N-(3,4-dichlorophenyl)-1,8,8-trimethyl-2,4-dioxobicyclo[3.2.1]octane-3-carboxamide;
(1R)-N-(3-nitrophenyl)-1,8,8-trimethyl-2,4-dioxobicyclo[3.2.1]octane-3-carboxamide;
(1R)-N-(4-nitrophenyl)-1,8,8-trimethyl-2,4-dioxobicyclo[3.2.1]octane-3-carboxamide;
(1R)-N-[4-chloro-3-(trifluoromethyl)phenyl]-1,8,8-trimethyl-2,4-dioxobicyclo[3.2.1]octane-3-carboxamide;
(1R)-N-[3-(trifluoromethyl)phenyl]-1,8,8-trimethyl-2,4-dioxobicyclo[3.2.1]octane-3-carboxamide;
(1R)-N-[4-(trifluoromethyl)phenyl]-1,8,8-trimethyl-2,4-dioxobicyclo[3.2.1]octane-3-carboxamide;
(1R)-N-[4-chlorophenyl]-1,8,8-trimethyl-2,4-dioxobicyclo[3.2.1]octane-3-carboxamide;
(1R)-N-[3-chloro-4-fluorophenyl]-1,8,8-trimethyl-2,4-dioxobicyclo[3.2.1]octane-3-carboxamide; or
(1R)-N-[4-fluoro-3-(trifluoromethyl)phenyl]-1,8,8-trimethyl-2,4-dioxobicyclo[3.2.1]octane-3-carboxamide;
(1R)-N-[4-methylphenyl]-1,8,8-trimethyl-2,4-dioxobicyclo[3.2.1]octane-3-carboxamide;
(1R)-N-[4-(dimethylamino)phenyl]-1,8,8-trimethyl-2,4-dioxobicyclo[3.2.1]octane-3-carboxamide; or
tautomers thereof, pharmaceutically acceptable salts thereof, or both.

Compounds of formula (I) can be synthesized in one step as outlined in Scheme I.

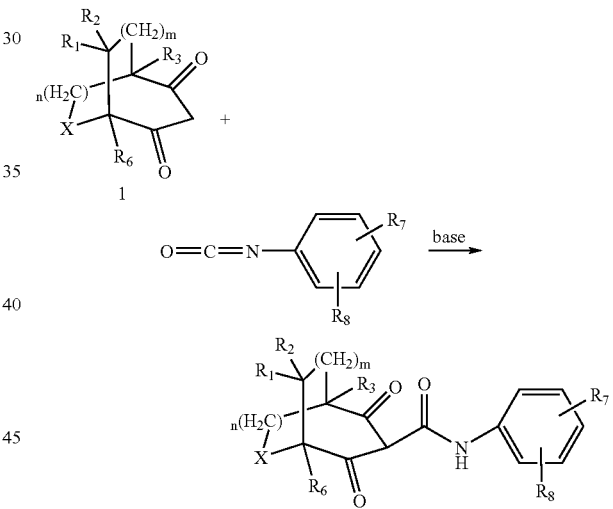

Scheme I

An appropriate bicyclic-1,3-dione (1) is treated with the desired arylisocyanate under basic catalysis to give the final product (2), which can be isolated and subsequently converted to a pharmaceutically acceptable salt. The base employed in this reaction can be, but is not limited to, a tertiary amine such as triethylamine or diisopropylethylamine (Hunig's Base) or a stronger base such as sodium methoxide, potassium t-butoxide, sodium hydride, or lithium diisopropylamide (LDA). If the base is a tertiary amine, an agent can be employed to facilitate the reaction. Examples of such facilitating agents include, but are not limited to, 4-(dimethylamino)-pyridine (DMAP). Reagents other than bases can be used to catalyze the reaction, such as transition metal complexes. Examples of suitable transition metal complexes include, but are not limited to, nickel (II) acetoacetate, copper (II) N,N-diethylacetoacetamide, and triethyllead methoxide.

Alternatively, the 1,3-dione (1) can be converted to an intermediate reactive salt species and then subsequently treated with the arylisocyanate to give the final product (2), as outlined in Scheme II:

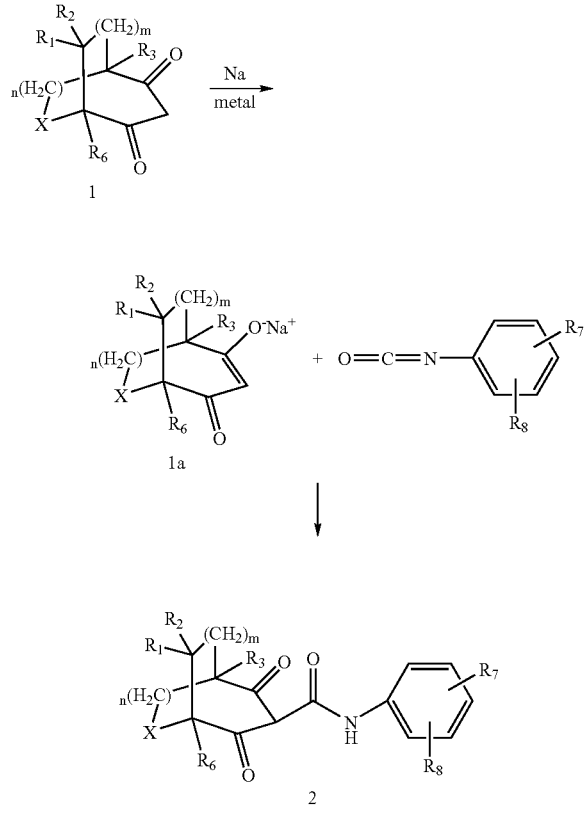

Here, an appropriate 1,3-dione (1) is first treated with a base or other reagent to give an intermediate reactive species (1a). This species is then reacted with the arylisocyanate to yield the desired product (2). Examples of suitable reagents for forming the intermediate reactive species include, but are not limited to, sodium metal and sodium hydride.

Another method for preparing the compounds of formula (I) involves treating the appropriate 1,3-dione (1) with phosgene or a phosgene equivalent in the presence of base catalysis (Scheme III), followed by reaction with an aniline to yield the desired product (2).

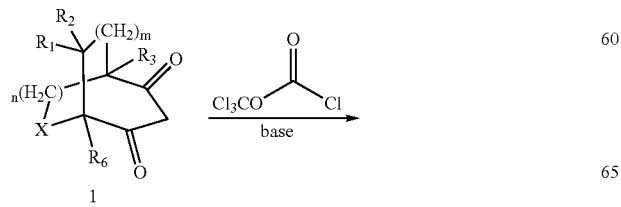

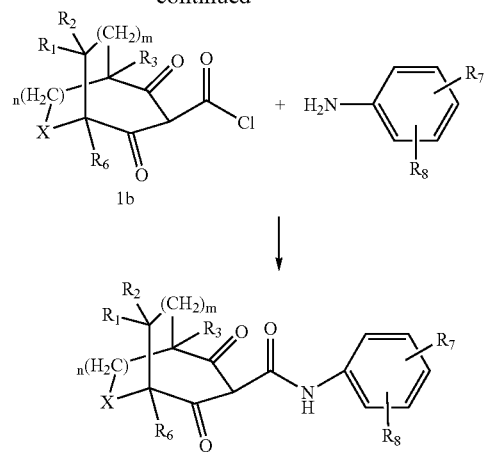

Suitable phosgene equivalents include, but are not limited to, trichloromethylchloroformate and triphosgene (bis(trichloromethyl)carbonate). Bases that can be used to catalyze this reaction include, but are not limited to, tertiary amine bases such as triethylamine and diisopropylethylamine (Hunig's base).

Examples of the bicyclic dione (1) include the following shown below:

(a)

(b)

(c)

(d)

-continued (e)
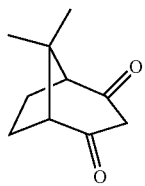

(f)
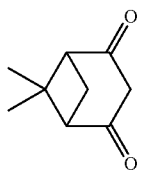

(g)
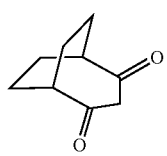

(h)
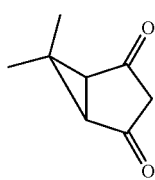

The bicyclic dione starting materials can be prepared, for example, via methods described in the literature or by procedures described herein. For example, commercially available (1R)-, (1S)- and racemic camphorquinone (H. Herzog, et al., *Synthesis*, 788–790 (1986); G. Helmchen, et al., *Tetrahedron Lett.*, 24, 3213-3216 (1983), and W. C. Evens and J. Chen., *J. Chem. Soc.*, 137 (1934), respectively) can be converted to 1,8,8-trimethylbicyclo[3.2.1]octane-2,4-dione (compounds (a) to (c) above) according to the procedure of Eistert, et al., (*Liebigs Ann. Chem.*, 64–82 (1962)). The desmethyl analog, bicyclo[3.2.1]octane-2,4-dione (compound (d) above), can be prepared via a sequence that involves oxidation of the readily available norbornanone (Hanack and Dolde, *Liebigs Ann. Chem.*, 1973, 1557–1570), followed by ring expansion using the method described by Eistert, et al. A similar reaction sequence can be applied to various known mono-methyl norbornanones (Berson, et al., *J. Am. Chem. Soc.*, 83, 3986–3997 (1961); Wiberg and Cunningham, *J. Org. Chem.*, 55, 679–684 (1990)) to prepare the corresponding mono-methyl bicyclo[3.2.1]octane-2,4-diones. The preparation of 8,8-dimethyl-bicyclo[3.2.1]octane-2,4-dione (compound (e)) has also been described in the literature (Cervantes, et al., Tetrahedron, 42, 3491–3502 (1986)). The syntheses of various bicyclo[3.1.1]heptane-2,4-diones have been reported as well (Beckmann and Ling, *Chem. Ber.*, 94, 1899–1960 (1961); Guha and Ganaphthi, *Chem. Ber.*, 69, 1185–1194 (1936)).

Alternatively, bicyclo[3.1.1]heptane-2,4-diones (such as compound (f)) can prepared by converting a compound of the following formula (II):

(II)

where $R_1$ to $R_6$ are as described previously, to the desired bicyclo[3.1.1]heptane-2,4-dione having the formula (III):

(III)

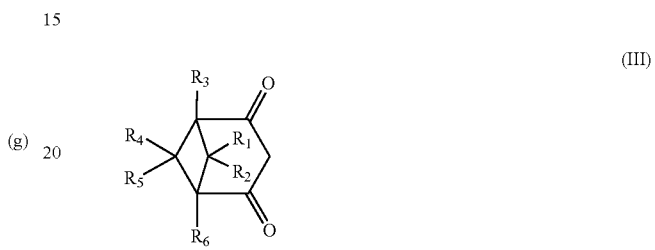

The compound of formula (II) is preferably contacted with a base such as NaH or other suitable isomerization catalyst to yield the isomer of formula (IIa):

(IIa)

The compound of formula (IIa) undergoes ozonolysis to form the bicyclo[3.1.1]heptane-2,4-dione of formula (III). For example, 6,6-dimethyl-bicyclo[3.1.1]heptane-2,4-dione (Intermediate I) can be prepared by a procedure illustrated in Scheme IV.

Scheme IV

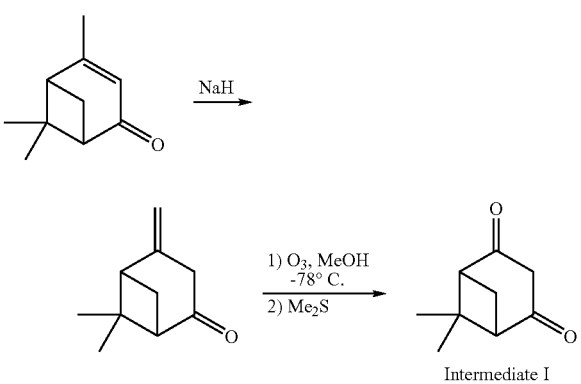

Intermediate I

In this procedure, 2(10)pinen-4-one is converted to the desired bicyclo[3.1.1]heptane-2,4-dione by ozonolysis. The pinene-4-one starting material can be obtained from commercially available verbanone by base-catalyzed isomerization using a published procedure (Ohloff and Giersch, *Helv. Chim. Acta,* 60, 1496–1500 (1977)).

The synthesis of bicyclo[3.2.2]nonane-2,4-dione (Intermediate II, compound (g) above) has been reported in the literature (Gleiter, et al., *Tet. Lett.,* 36, 655–659 (1980)). Bicyclo[3.2.2]nonane-2,4-dione can be obtained from the corresponding quinone using the ring expansion procedure of Eistert, et al., according to Scheme V.

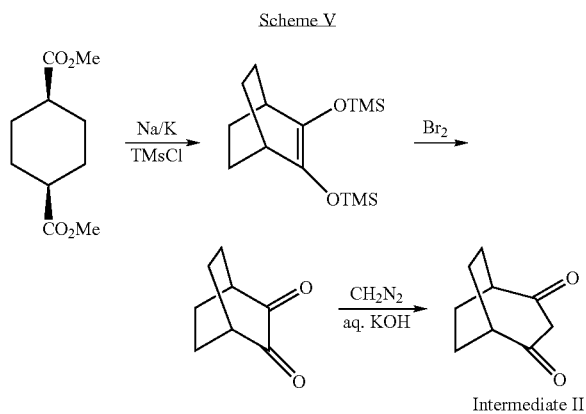

Intermediate II

The quinone starting material, bicyclo[2.2.2]octane-2,3-dione, can be prepared according to the methodology of Reddy et al. (*J. Org. Chem.,* 58, 7622–7623 (1993)) from cis-methyl-1,4-cyclohexane carboxylate in a two step sequence that involves, 1) acyloin condensation in the presence of Na/K alloy and chlorotrimethylsilane, and 2) removal of the trimethylsilyl groups and oxidation of the acyloin to the quinone with bromine.

The 6,6-dimethyl-bicyclo[3.1.0]hexane-2,4-dione (compound (h)) can be prepared by a procedure reported in the literature (Milewska, et al., *Tetrahedron., Asymmetry,* 7, 3169–3180 (1996); Friedrick, *Synthesis,* 368–369 (1970)), starting with ethyl chrysanthemate.

As mentioned previously, the compounds of the present invention activate or inhibit the inactivation of Kv1.1 voltage-gated potassium channels in a mammal. The compounds are especially useful for inhibiting the inactivation of Kv1.1/Kvβ1 voltage-gated potassium channels. The compounds of formula (I) are preferably useful for inhibiting N-type inactivation of Kv1.1 voltage-gated potassium channels.

Accordingly, the present invention relates to in vitro or in vivo methods of modulating the activity of the Kv1.1 voltage-gated potassium channel. Such methods comprise, in some embodiments of the invention, contacting Kv1.1 voltage-gated potassium channel with a compound of formula (I). In certain embodiments, such methods further comprise monitoring the activity of Kv1.1. In certain embodiments of the invention, the invention relates to methods of modulating the activity of the Kv1.1 voltage-gated potassium channel comprising in vitro or in vivo administration of a therapeutically effective amount of one or more compounds of formula (I).

In other embodiments, the invention relates to in vitro or in vivo methods of inhibiting the inactivation of, or activating the Kv1.1 voltage-gated potassium channel. Such methods comprise, in some embodiments of the invention, contacting Kv1.1 with a compound of formula (I). In certain embodiments, such methods further comprise monitoring the activity of Kv1.1. In certain embodiments of the invention, the invention relates to methods of inhibiting the inactivation of, or activating the Kv1.1 voltage-gated potassium channel comprising in vitro or in vivo administration of an effective amount of one or more compounds of formula (I).

The compounds of formula (I) are useful for treating a variety of conditions in a mammal associated with the abnormal inactivation (including decreased activation) of Kv1.1 voltage-gated potassium channels. Conditions that are believed to be associated with the inactivation of voltage gated potassium channels include for example conditions associated with neuronal hyperexcitability, abnormal glutamate regulation, epilepsy, stroke, convulsions, or anxiety disorders, or combinations thereof. In a preferred embodiment of the present invention, the condition treated is epilepsy or stroke.

Conditions associated with neuronal hyperexcitability that can be treated in accordance with the methods of the present invention include for example convulsions, including neonatal convulsions, epilepsy, episodic ataxia, myokymia, cerebral ischemia, cerebral palsy, stroke, traumatic brain injury, traumatic spinal cord injury, asphyxia, anoxia or prolonged cardiac surgery or combinations thereof.

Conditions associated with the abnormal regulation of glutamate include for example hypoglycemia or diseases associated with abnormal glutamate regulation such as Parkinson's disease, Huntingdon's disease, Alzheimer's disease, amyotrophic lateral sclerosis, or AIDS related dementia or combinations thereof.

Another condition associated with the abnormal regulation of glutamate is pain experienced by mammals. For example, the compounds of the present invention may be used for treating acute pain (short duration) or chronic pain (regularly reoccurring or persistent) in mammals. This pain may also be centralized or peripheral.

Examples of pain that can be acute or chronic and that can be treated in accordance with the methods of the present invention include inflammatory pain, musculoskeletal pain, bony pain, lumbosacral pain, neck or upper back pain, visceral pain, somatic pain, neuropathic pain, cancer pain, pain caused by injury or surgery such as burn pain, or headaches such as migraines or tension headaches, or combinations of these pains. One skilled in the art will recognize that these pains may overlap one another. For example, a pain caused by inflammation may also be visceral or musculoskeletal in nature.

In some embodiments of the present invention the compounds are administered in mammals to treat chronic pain such as neuropathic pain associated for example with damage to or pathological changes in the peripheral or central nervous systems; cancer pain; visceral pain associated with for example the abdominal, pelvic, and/or perineal regions or pancreatitis; musculoskeletal pain associated with for example the lower or upper back, spine, fibromylagia, temporomandibular joint, or myofascial pain syndrome; bony pain associated with for example bone or joint degenerating disorders such as osteoarthritis, rheumatoid arthritis, or spinal stenosis; headaches such migraine or tension headaches; or pain associated with infections such as HIV or Shingles, sickle cell anemia, autoimmune disorders, multiple sclerosis, or inflammation such as osteoarthritis or rheumatoid arthritis. One skilled in the art will also recognize that the pain treated according to the methods of the present invention may also be related to conditions of hyperalgesia, allodynia, or both. Additionally, the chronic pain may be with or without peripheral or central sensitization.

Additional conditions associated with Kv1.1 inactivation that may be treated in accordance with the methods of the present invention include anxiety disorders such as panic attack, agoraphobia, panic disorder, specific phobia, social phobia, obsessive compulsive disorder, posttraumatic stress disorder, acute stress disorder, generalized anxiety disorder, separation anxiety disorder, substance-induced anxiety disorder, and anxiety disorder not otherwise specified.

Thus the present invention provides methods of treating each of the conditions listed above in a mammal, preferably in a human, the methods comprising administering a therapeutically effective amount of a compound of this invention to the mammal in need thereof. The term "administer" or "administering" includes administering the compound or pharmaceutical composition indirectly via a prodrug derivative or analog which will form an equivalent amount of the active compound or substance within the body.

Thus, the present invention includes prodrugs of compounds of Formula I. Prodrug, as used herein, means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113–191 (1991), Bundgaard, et al., Journal of Drug Delivery Reviews, 8:1–38 (1992), Bundgaard, J. of Pharmaceutical Sciences, 77:285 et seq. (1988); and Higuchi and Stella (eds.) Prodrugs as Novel Drug Delivery Systems, American Chemical Society (1975).

The bicyclic amide derivatives useful in the present invention can be administered in a variety of ways including for example by oral or parenteral administration such as by intramuscular, intraperitoneal, epidural, intrathecal, intravenous, subcutaneous, intramucosal such as sublingual or intranasal, vaginal, rectal or transdermal administration. In a preferred embodiment of the present invention, the compounds useful in the present invention are administered by oral or intranasal route.

The compounds useful in the present invention are administered in a therapeutically effective amount to the mammal needing treatment. The therapeutically effective amount is the amount of the bicyclic amide derivative or a pharmaceutically acceptable salt form thereof, which at least partially treats the condition in question in a mammal. The therapeutically effective amount will depend on such variables as the particular composition used, the route of administration, the severity of the symptoms, and the particular patient being treated. To determine the therapeutically effective amount of the compound to be administered, the physician may, for example, evaluate the effects of a given bicyclic amide derivative in the patient by incrementally increasing the dosage until the desired symptomatic relief level is achieved. The continuing dose regimen may then be modified to achieve the desired result.

The bicyclic amide derivatives of the present invention may be administered neat (i.e., as is) or in a pharmaceutical composition containing at least one pharmaceutically acceptable carrier. Thus, the present invention also provides pharmaceutical compositions containing a therapeutically effective amount of at least one compound of formula I or a tautomer thereof or pharmaceutically acceptable salt thereof, or both, and at least one pharmaceutically acceptable carrier.

Preferred compounds to be present in the pharmaceutical compositions of the present invention include those compounds of formula (I) previously described herein. Pharmaceutically acceptable carriers are those that are compatible with the other ingredients in the formulation and biologically acceptable. The pharmaceutical compositions may be administered to a mammal to treat a variety of conditions as previously described herein.

Pharmaceutical compositions useful in the present invention may be in any form known to those skilled in the art such as in liquid or solid form. The proportion of ingredients will depend on such factors as the solubility and chemical nature of the compound of formula I and the chosen route of administration. Such compositions are prepared in accordance with acceptable pharmaceutical procedures, such as described in *Remingtons Pharmaceutical Sciences*, 17th edition, ed. Alfonoso R. Gennaro, Mack Publishing Company, Easton, Pa. (1985).

Pharmaceutical compositions, in addition to containing a therapeutically effective amount of one or more bicyclic amide derivatives of the present invention and a pharmaceutically acceptable carrier may include one or more other ingredients known to those skilled in the art for formulating pharmaceutical compositions. Such ingredients include for example, flavoring agents, lubricants, solubilizers, suspending agents, fillers, glidants, compression aids, binders, tablet-disintegrating agents, encapsulating materials, emulsifiers, buffers, preservatives, sweeteners, thickening agents, coloring agents, viscosity regulators, stabilizers or osmo-regulators, or combinations thereof.

In some embodiments, the solid pharmaceutical compositions may contain one or more solid carriers, and optionally one or more other additives such as flavoring agents, lubricants, solubilizers, suspending agents, fillers, glidants, compression aids, binders or tablet-disintegrating agents or an encapsulating material. One skilled in the art will recognize that some of these other additives also serve as carriers. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes or ion exchange resins, or combinations thereof. In powder pharmaceutical compositions, the carrier is preferably a finely divided solid which is in admixture with the finely divided active ingredient. In tablets, the active ingredient is mixed with a carrier having the necessary compression properties in suitable proportions, and optionally, other additives, and compacted into the desired shape and size. Solid pharmaceutical compositions, such as powders and tablets, preferably contain up to 99% of the active ingredient.

In other embodiments, liquid pharmaceutical compositions may contain one or more bicyclic amide derivatives and one or more liquid carriers to form for example solutions, suspensions, emulsions, syrups, elixirs, or pressurized compositions. Pharmaceutically acceptable liquid carriers include for example water, organic solvent, pharmaceutically acceptable oils or fat, or combinations thereof. The pharmaceutical composition can contain other suitable pharmaceutical additives such as solubilizers, emulsifiers, buffers, preservatives, sweeteners, flavoring agents, suspending agents, thickening agents, colors, viscosity regulators, stabilizers or osmo-regulators, or combinations thereof. One skilled in the art will recognize that some of these other additives also serve as carriers.

Examples of liquid carriers suitable for oral or parenteral administration include water (preferably containing additives such as cellulose derivatives such as sodium carboxymethyl cellulose), alcohols or their derivatives (including monohydric alcohols or polyhydric alcohols such as glycols) or oils (e.g., fractionated coconut oil and arachis oil). For parenteral administration the carrier can also be an oily ester such as ethyl oleate and isopropyl myristate. The liquid carrier for pressurized compositions can be halogenated hydrocarbons or other pharmaceutically acceptable propellant.

Liquid pharmaceutical compositions which are sterile solutions or suspensions can be administered parenterally, for example by, intramuscular, intraperitoneal, epidural, intrathecal, intravenous or subcutaneous injection. Pharmaceutical compositions for oral or transmucosal administration may be either in liquid or solid composition form.

The compounds of this invention may be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

In some embodiments, the pharmaceutical composition may be in unit dosage form, such as tablets or capsules. In such form, the composition is sub-divided in unit dose containing appropriate quantities of the active ingredient. The unit dosage forms can be packaged compositions, for example packeted powders, vials, ampoules, pre-filled syringes or sachets containing liquids. The unit dosage form can be, for example, a capsule or tablet itself, or it can be the appropriate number of any such compositions in package form.

Thus, the present invention also provides a pharmaceutical composition in unit dosage form that contains a therapeutically effective unit dosage of at least one bicyclic amide derivative of the present invention. As one skilled in the art will recognize, the preferred therapeutically effective unit dosage will depend on for example the method of administration.

EXAMPLES

Compounds of the present invention were prepared and evaluated for inhibiting the inactivation of voltage-gated potassium channels and for inhibiting seizures and anxiety.

The following compounds of formula (I) were prepared. In these examples, all chemicals and intermediates are either commercially available, can be prepared by standard procedures found in the literature, and/or their synthesis is described herein.

Intermediate I: 6,6-dimethyl-bicyclo[3.1.1]heptane-2,4-dione

A solution of 6,6-dimethyl-4-methylene-bicyclo[3.1.1] heptan-2-one (2(10)pinen-4-one, 6.8 g, 45.3 mmol) in dry methanol (300 mL) under a nitrogen atmosphere was cooled to −78° C. in a dry ice/acetone bath. The stirred reaction was treated with ozone for 20 minutes, during which time the solution turned a light blue color, indicating accumulation of ozone and completion of the reaction. The reaction was purged with oxygen (5 minutes), followed by nitrogen (10 minutes) at −78° C., and then dimethyl sulfide (5.0 ml, 68.2 mmole) was added dropwise via a syringe. The resulting reaction mixture was stirred overnight, during which time it came up to room temperature. Methanol was removed on a rotary evaporator, and the residue was partitioned between ethyl acetate (300 mL) and water (300 mL). The aqueous layer was extracted with two additional portions of ethyl acetate (300 mL), and the combined organic layers were dried over anhydrous sodium sulfate and concentrated on a rotary evaporator. The desired product was isolated by column chromatography on silica gel (20% ethyl acetate/hexane) to gave the desired product as a white solid (5.7 g; 83% yield), mp=80–81° C.; MS (−) ESI m/z=151 (M−H)⁻.

Analysis for $C_9H_{12}O_2$ Calculated: C: 71.03; H, 7.95. Found: C: 70.80; H, 7.86.

Intermediate II: Bicyclo[3.2.2]nonane-2,4-dione

To a magnetically stirred mixture of diethyl ether (95 mL) and 25% aqueous sodium hydroxide solution (60 mL) cooled to ° 0 C in a 500 mL Erlenmeyer flask, N-methyl-N-nitrosourea (4.2 g, 40.6 mmol) was added in three equal portions at one hour intervals. The organic layer assumed a yellow color during the addition, indicating the presence of diazomethane. Upon complete addition of the N-methyl-N-nitrosourea, the reaction mixture was stirred at ° 0 C. for an additional 3 hours. The yellow organic layer was decanted into another 500 mL Erlenmeyer flask containing a 5% aqueous potassium hydroxide solution (20 mL) that had been previously cooled in an ice bath. To the ice-cooled two-phase mixture was added a solution of bicyclo[2.2.2] octane-2,4-dione (0.70 g, 5.1 mmol) in diethyl ether (15 mL). The resulting reaction mixture was stirred overnight, during which time it came up to room temperature and the yellow color disappeared. The mixture was concentrated on a rotary evaporator and the aqueous residue was made acidic by addition of concentrated HCl. The resulting cloudy white mixture was extracted with three potions of dichloromethane (40 mL). The combined organic layers were dried over anhydrous sodium sulfate and concentrated on a rotary evaporator to yield a light yellow solid. Recrystallization of the yellow solid from ethyl acetate/hexane provided the desired product as and off-white solid (0.45 g, 58% yield), mp=170–172° C.; MS (−) ESI m/z=151 (M−H)⁻.

Analysis for $C_9H_{12}O_2$ Calculated: C: 71.03; H, 7.95. Found: C: 70.72; H, 7.95.

Example 1

(1S)-N-[3,5-bis(trifluoromethyl)phenyl]-1,8,8-trimethyl-2,4-dioxobicyclo[3.2.1] octane-3-carboxamide To an ice-cooled solution of (1S)-1,8,8-trimethylbicyclo [3.2.1]octane-2,4-dione (0.36 g, 2.0 mmole), triethylamine (0.20 g, 2.0 mmole) and 4-(dimethylamino)pyridine (0.24 g, 2.0 mmole) in dry dichloromethane (25 mL) was added a solution of 3,5-bis-(trifluoromethyl)phenyl isocyanate (0.51 g, 2.0 mmole) in dry dichloromethane (5 mL). The resulting mixture was allowed to stir overnight under a nitrogen atmosphere, during which time it came up to room temperature, and then was heated at 30° C. for 7 hours. The reaction mixture was treated with 2N aqueous HCl and the layers separated. The acidic aqueous layer was extracted with two additional portions of dichloromethane. The combined organic layers were dried over anhydrous sodium sulfate and concentrated on a rotary evaporator to give a yellow oil, which was purified by chromatography on silica gel (10% ethyl acetate/hexane) to yield a yellow oil, which was crystallized from 95% ethanol to yield the title compound as a beige solid (0.36 g, 42% yield), mp=68–72° C.; MS (−) ESI m/z=434 (M−H)$^-$; $[\alpha]_D^{25}$=−21.0° (c=1, EtOH).

Analysis for $C_{20}H_{19}F_6NO_3$ Calculated: C: 55.18; H, 4.40; N, 3.22. Found: C: 55.43; H, 4.28; N, 3.12.

Example 2

(1S)-N-[3-(trifluoromethyl)phenyl]-1,8,8-trimethyl-2,4-dioxobicyclo[3.2.1] octane-3-carboxamide To an ice-cooled solution of (1S)-1,8,8-trimethylbicyclo [3.2.1]octane-2,4-dione (0.36 g, 2.0 mmole), triethylamine (0.20 g, 2.0 mmole) and 4-(dimethylamino)pyridine (0.24 g, 2.0 mmole) in dry dichloromethane (25 mL) was added a solution of 3-(trifluoromethyl)phenyl isocyanate (0.37 g, 2.0 mmole) in dry dichloromethane (5 mL). The resulting mixture was allowed to stir overnight under a nitrogen atmosphere, during which time it came up to room temperature, and then was heated at 30° C. for 7 hours. The reaction mixture was treated with 2N aqueous HCl and the layers separated. The acidic aqueous layer was extracted with two additional portions of dichloromethane. The combined organic layers were dried over anhydrous sodium sulfate and concentrated on a rotary evaporator to give a yellow oil, which was purified by chromatography on silica gel (10% ethyl acetate/hexane) to yield a yellow oil, which was crystallized from 95% ethanol to yield the title compound as a beige solid (0.30 g, 41% yield), mp=60–62° C.; MS (−) ESI m/z=366 (M−H)$^-$; $[\alpha]_D^{25}$=−22.0° (c=1, EtOH).

Analysis for $C_{19}H_{20}F_3NO_3$ Calculated: C: 62.12; H, 5.49; N, 3.81. Found: C: 61.77; H, 5.28; N, 3.76.

Example 3

(1S)-N-(3,5-dichlorophenyl)-1,8,8-trimethyl-2,4-dioxobicyclo[3.2.1]octane-3-carboxamide To an ice-cooled solution of (1S)-1,8,8-trimethylbicyclo [3.2.1]octane-2,4-dione (0.18 g, 1.0 mmole), triethylamine (0.10 g, 1.0 mmole) and 4-(dimethylamino)pyridine (0.12 g, 1.0 mmole) in dry dichloromethane (25 mL) was added a solution of 3,5dichlorophenyl isocyanate (0.19 g, 1.0 mmole) in dry dichloromethane (5 mL). The resulting mixture was allowed to stir overnight under a nitrogen atmosphere, during which time it came up to room temperature, and then was heated at 30° C. for 7 hours. The reaction mixture was treated with 2N aqueous HCl and the layers separated. The acidic aqueous layer was extracted with two additional portions of dichloromethane. The combined organic layers were dried over anhydrous sodium sulfate and concentrated on a rotary evaporator to give a yellow oil, which was purified by chromatography on silica gel (10% ethyl acetate/hexane) to yield a yellow oil, which was crystallized from 95% ethanol to yield the title compound as a beige solid (0.20 g, 55% yield), mp=112–114° C.; MS (−) ESI m/z=366 (M−H)$^-$; $[\alpha]_D^{25}$=−25.4° (c=1, EtOH).

Analysis for $C_{18}H_{19}C_2NO_3$ Calculated: C: 58.71; H, 5.20; N, 3.80. Found: C: 58.57; H, 4.96; N, 3.68.

Example 4

(1S)-N-(3,4-dichlorophenyl)-1,8,8-trimethyl-2,4-dioxobicyclo[3.2.1]octane-3-carboxamide To an ice-cooled solution of (1S)-1,8,8-trimethylbicyclo [3.2.1]octane-2,4-dione (0.18 g, 1.0 mmole), triethylamine (0.10 g, 1.0 mmole) and 4-(dimethylamino)pyridine (0.12 g, 1.0 mmole) in dry dichloromethane (25 mL) was added a solution of 3,4-dichlorophenyl isocyanate (0.19 g, 1.0 mmole) in dry dichloromethane (5 mL). The resulting mixture was allowed to stir overnight under a nitrogen atmosphere, during which time it came up to room temperature, and then was heated at 30° C. for 7 hours. The reaction mixture was treated with 2N aqueous HCl and the layers separated. The acidic aqueous layer was extracted with two additional portions of dichloromethane. The combined organic layers were dried over anhydrous sodium sulfate and concentrated on a rotary evaporator to give a yellow oil, which was purified by chromatography on silica gel (10% ethyl acetate/hexane) to yield a yellow oil, which was crystallized from 95% ethanol to yield the title compound as a tan solid (0.21 g, 57% yield), mp=88–90° C.; MS (−) ESI m/z=366 (M−H)$^-$; $[\alpha]_D^{25}$=−24.8° (c=1, EtOH).

Analysis for $C_{18}H_{19}Cl_2NO_3$ Calculated: C: 58.71; H, 5.20; N, 3.80. Found: C: 59.06; H, 5.23; N, 3.54.

Example 5

(1S)-N-(3-nitrophenyl)-1,8,8-trimethyl-2,4-dioxobicyclo[3.2.1]octane-3-carboxamide To an ice-cooled solution of (1S)-1,8,8-trimethylbicyclo [3.2.1]octane-2,4-dione (0.36 g, 2.0 mmole), triethylamine (0.20 g, 2.0 mmole) and 4-(dimethylamino)pyridine (0.24 g, 2.0 mmole) in dry dichloromethane (25 mL) was added a solution of 3-nitrophenyl isocyanate (0.33 g, 2.0 mmole) in dry dichloromethane (5 mL). The resulting mixture was allowed to stir overnight under a nitrogen atmosphere, during which time it came up to room temperature, and then was heated at 30° C. for 72 hours. The reaction mixture was treated with 2N aqueous HCl and the layers separated. The acidic aqueous layer was extracted with two additional portions of dichloromethane. The combined organic layers were dried over anhydrous sodium sulfate and concentrated on a rotary evaporator to give a yellow oil, which was purified by chromatography on silica gel (10% ethyl acetate/ hexane) to yield an orange oil, which was crystallized from 95% ethanol to yield the title compound as a beige solid (0.20 g, 29% yield), mp=100–102° C.; MS (−) ESI m/z=343 (M−H)$^-$; $[\alpha]_D^{25}$=−26.3° (c=1, DMSO).

Analysis for $C_{18}H_{20}N_2O_5$ Calculated: C: 62.78; H, 5.85; N, 8.13. Found: C: 62.77; H, 5.78; N, 8.28.

Example 6

(1S)-N-(4-nitrophenyl)-1,8,8-trimethyl-2,4-dioxobicyclo[3.2.1]octane-3-carboxamide To an ice-cooled solution of (1S)-1,8,8-trimethylbicyclo [3.2.1]octane-2,4-dione (0.36 g, 2.0 mmole), triethylamine (0.20 g, 2.0 mmole) and 4-(dimethylamino)pyridine (0.24 g, 2.0 mmole) in dry dichloromethane (25 mL) was added a solution of 4-nitrophenyl isocyanate (0.33 g, 2.0 mmole) in dry dichloromethane (5 mL). The resulting mixture was allowed to stir overnight under a nitrogen atmosphere, during which time it came up to room temperature, and then was heated at 30° C. for 48 hours. The reaction mixture was treated with 2N aqueous HCl and the layers separated. The acidic aqueous layer was extracted with two additional portions of dichloromethane. The combined organic layers were dried over anhydrous sodium sulfate and concentrated on a rotary evaporator to give a yellow oil, which was purified by chromatography on silica gel (10% ethyl acetate/ hexane) to yield an orange oil, which was crystallized from 95% ethanol to yield the title compound as a beige solid (0.29 g, 42% yield), mp=170–172° C.; MS (−) ESI m/z=343 (M−H)$^-$; $[\alpha]_D^{25}$=−33.4° (c=1, DMSO).

Analysis for $C_{18}H_{20}N_2O_5$ Calculated: C: 62.78; H, 5.85; N, 8.13. Found: C: 62.88; H, 5.74; N, 8.10.

Example 7

(1S)-N-[4-chloro-3-(trifluoromethyl)phenyl]-1,8,8-trimethyl-2,4-dioxobicyclo [3.2.1]octane-3-carboxamide To an ice-cooled solution of (1S)-1,8,8-trimethylbicyclo [3.2.1]octane-2,4-dione (0.18 g, 1.0 mmole), triethylamine (0.10 g, 1.0 mmole) and 4-(dimethylamino)pyridine (0.12 g, 1.0 mmole) in dry dichloromethane (25 mL) was added a solution of 4-chloro-3-(trifluoromethyl)phenyl isocyanate (0.22 g, 1.0 mmole) in dry dichloromethane (5 mL). The resulting mixture was allowed to stir overnight under a nitrogen atmosphere, during which time it came up to room temperature, and then was heated at 30° C. for 7 hours. The reaction mixture was treated with 2N aqueous HCl and the layers separated. The acidic aqueous layer was extracted with two additional portions of dichloromethane. The combined organic layers were dried over anhydrous sodium sulfate and concentrated on a rotary evaporator to give a yellow oil, which was purified by chromatography on silica gel (10% ethyl acetate/hexane) to yield a yellow oil, which was crystallized from 95% ethanol to yield the title compound as an off-white solid (0.21 g, 51% yield), mp=118–120° C.; MS (+) ESI m/z=402 (M+H)$^+$, $[\alpha]_D^{25}$=−23.7° (c=1, EtOH).

Analysis for $C_{18}H_{19}ClF_3NO_3$ Calculated: C: 56.79; H, 4.77; N, 3.49. Found: C: 56.70; H, 4.64; N, 3.46.

Example 8

(1S)-N-[4-(trifluoromethyl)phenyl]-1,8,8-trimethyl-2,4-dioxobicyclo[3.2.1] octane-3-carboxamide To an ice-cooled solution of (1S)-1,8,8-trimethylbicyclo [3.2.1]octane-2,4-dione (0.36 g, 2.0 mmole), triethylamine (0.20 g, 2.0 mmole) and 4-(dimethylamino)pyridine (0.24 g, 2.0 mmole) in dry dichloromethane (20 mL) was added a solution of 4-(trifluoromethyl)phenyl isocyanate (0.41 g, 2.2 mmole) in dry dichloromethane (3 mL). The resulting reaction mixture was allowed to stir overnight under a nitrogen atmosphere, during which time it came up to room temperature. The resulting mixture was concentrated on a rotary evaporator and then partitioned between dichloromethane and 2N aqueous HCl. The acidic aqueous layer was extracted with two additional portions of dichloromethane. The combined organic layers were dried over anhydrous sodium sulfate and concentrated on a rotary evaporator to give a yellow oil, which was purified by chromatography on silica gel (10% ethyl acetate/hexane) to yield the title compound as an orange solid (0.36 g, 49% yield), mp=81–83° C.; MS (−) ESI m/z=366 (M−H)$^-$; $[\alpha]_D^{25}$=−25.6° (c=1, EtOH).

Analysis for $C_{19}H_{20}F_3NO_3$ Calculated: C: 62.12; H, 5.49; N, 3.81. Found: C: 62.41; H, 5.66; N, 3.96.

Example 9

(1S)-N-[4-(dimethylamino)phenyl]-1,8,8-trimethyl-2,4-dioxobicyclo[3.2.1] octane-3-carboxamide To an ice-cooled solution of (1S)-1,8,8-trimethylbicyclo [3.2.1]octane-2,4-dione (0.36 g, 2.0 mmole), triethylamine (0.20 g, 2.0 mmole) and 4-(dimethylamino)pyridine (0.24 g, 2.0 mmole) in dry dichloromethane (25 mL) was added a solution of 4-(dimethylamino)phenyl isocyanate (0.32 g, 2.0 mmole) in dry dichloromethane (5 mL). The resulting reaction mixture was allowed to stir overnight under a nitrogen atmosphere, during which time it came up to room temperature. It was then stirred at 30° C. for seven hours. The resulting mixture was treated with 2N aqueous HCl (30 mL) and the layers were separated. The acidic aqueous layer was extracted with two additional portions of dichloromethane (50 mL). The combined organic layers were dried over anhydrous sodium sulfate and concentrated on a rotary evaporator. The desired product was isolated by chromatography on silica gel (10% ethyl acetate/hexane) and recrystallized from 95% ethanol to yield the title compound as a light gray solid (0.16 g, 23% yield), mp=93–95° C.; MS (−) ESI m/z=341 (M−H)$^-$; $[\alpha]_D^{25}$=−23.8° (c=1, EtOH).

Analysis for $C_{20}H_{26}N_2O_3$ Calculated: C: 70.15; H, 7.65; N, 8.18. Found: C: 70.11; H, 7.79; N, 7.73.

Example 10

(1S)-N-[3-chloro-4-fluorophenyl]-1,8,8-trimethyl-2,4-dioxobicyclo[3.2.1] octane-3-carboxamide To an ice-cooled solution of (1S)1,8,8-trimethylbicyclo [3.2.1]octane-2,4-dione (0.18 g, 1.0 mmole), triethylamine (0.10 g, 1.0 mmole) and 4-(dimethylamino)pyridine (0.12 g, 1.0 mmole) in dry dichloromethane (25 mL) was added a solution of 3-chloro-4-fluorophenyl isocyanate (0.17 g, 1.0 mmole) in dry dichloromethane (5 mL). The resulting reaction mixture was allowed to stir overnight under a nitrogen atmosphere, during which time it came up to room temperature. It was then stirred at 30° C. for seven hours. The resulting mixture was treated with 2N aqueous HCl (30 mL) and the layers were separated. The aqueous layer was extracted with two additional portions of dichloromethane (50 mL). The combined organic layers were dried over anhydrous sodium sulfate and concentrated on a rotary evaporator. The desired product was isolated by chromatography on silica gel (10% ethyl acetate/hexane) and recrystallized from 95% ethanol to yield the title compound as a light orange solid (0.16 g, 47% yield), mp=87–89° C.; MS (−) ESI m/z=352 (M−H)$^-$; $[\alpha]_D^{25}$=−23.1° (c=1, EtOH).

Analysis for $C_{18}H_{19}ClFNO_3$ Calculated: C: 61.45; H, 5.44; N, 3.98. Found: C: 61.87; H, 5.58; N, 3.84.

Example 11

(1S)-N-[4-methylphenyl]-1,8,8-trimethyl-2,4-dioxobicyclo[3.2.1]octane-3-carboxamide To an ice-cooled solution of (1S)-1,8,8-trimethylbicyclo [3.2.1]octane-2,4-dione (0.36 g, 2.0 mmole), triethylamine (0.20 g, 2.0 mmole) and 4-(dimethylamino)pyridine (0.24 g, 2.0 mmole) in dry dichloromethane (25 mL) was added a solution of 4-methylphenyl isocyanate (0.27 g, 2.0 mmole) in dry dichloromethane (5 mL). The resulting reaction mixture was allowed to stir overnight under a nitrogen atmosphere, during which time it came up to room temperature. It was then stirred at 30° C. for seven hours. The resulting mixture was treated with 2N aqueous HCl (30 mL) and the layers were separated. The aqueous layer was extracted with two additional portions of dichloromethane (50 mL). The combined organic layers were dried over anhydrous sodium sulfate and concentrated on a rotary evaporator. The desired product was isolated by chromatography on silica gel (10% ethyl acetate/hexane) and recrystallized from 95% ethanol to yield the title compound as a brown solid (0.19 g, 30% yield), mp=80–82° C.; MS (−) ESI m/z=341 (M−H)$^-$; $[\alpha]_D^{25}$=−24.0° (c=1, EtOH).

Analysis for $C_{19}H_{23}NO_3$ Calculated: C: 72.82; H, 7.40; N, 4.47. Found: C: 72.43; H, 7.19; N, 4.59.

Example 12

(1R)-N-[3,5-bis(trifluoromethyl)phenyl]-1,8,8-trimethyl-2,4-dioxobicyclo [3.2.1]octane-3-carboxamide To an ice-cooled solution of (1R)-1,8,8-trimethylbicyclo [3.2.1]octane-2,4-dione (0.36 g, 2.0 mmole), triethylamine (0.20 g, 2.0 mmole) and 4-(dimethylamino)pyridine (0.24 g, 2.0 mmole) in dry dichloromethane (25 mL) was added a solution of 3,5-bis-(trifluoromethyl)phenyl isocyanate (0.51 g, 2.0 mmole) in dry dichloromethane (5 mL). The resulting mixture was allowed to stir overnight under a nitrogen atmosphere, during which time it came up to room temperature, and then was heated at 30° C. for 7 hours. The reaction mixture was treated with 2N aqueous HCl and the layers separated. The acidic aqueous layer was extracted with two additional portions of dichloromethane. The combined organic layers were dried over anhydrous sodium sulfate and concentrated on a rotary evaporator to give a yellow oil, which was purified by chromatography on silica gel (10% ethyl acetate/hexane) to yield a yellow oil, which was crystallized from 95% ethanol to yield the title compound as a yellow solid (0.44 g, 51% yield), mp=68–71° C.; MS (−) ESI m/z=434 (M−H)$^-$; $[\alpha]_D^{25}$=+22.8° (c=1, EtOH).

Analysis for $C_{20}H_{19}F_6NO_3$ Calculated: C: 55.18; H, 4.40; N, 3.22. Found: C: 54.99; H, 4.25; N, 3.95.

Example 13

(1R)-N-(3,5-dichlorophenyl)-1,8,8-trimethyl-2,4-dioxobicyclo[3.2.1]octane-3-carboxamide To an ice-cooled solution of (1R)-1,8,8-trimethylbicyclo [3.2.1]octane-2,4-dione (0.18 g, 1.0 mmole), triethylamine (0.10 g, 1.0 mmole) and 4-(dimethylamino)pyridine (0.12 g, 1.0 mmole) in dry dichloromethane (25 mL) was added a solution of 3,5-dichlorophenyl isocyanate (0.19 g, 1.0 mmole) in dry dichloromethane (5 mL). The resulting mixture was allowed to stir overnight under a nitrogen atmosphere, during which time it came up to room temperature, and then was heated at 30° C. for 24 hours. The reaction mixture was treated with 2N aqueous HCl and the layers separated. The acidic aqueous layer was extracted with two additional portions of dichloromethane. The combined organic layers were dried over anhydrous sodium sulfate and concentrated on a rotary evaporator to give a yellow oil, which was purified by chromatography on silica gel (10% ethyl acetate/hexane) to yield a yellow oil, which was crystallized from 95% ethanol to yield the title compound as a white solid (0.25 g, 67% yield), mp=115–117° C.; MS (−) ESI m/z=366 (M−H)$^-$; $[\alpha]_D^{25}$=+24.9° (c=1, EtOH).

Analysis for $C_{18}H_{19}Cl_2NO_3$ Calculated: C: 58.71; H, 5.20; N, 3.80. Found: C: 58.67; H, 5.18; N, 3.57.

Example 14

(1R)-N-(3,4-dichlorophenyl)-1,8,8-trimethyl-2,4-dioxobicyclo[3.2.1]octane-3-carboxamide To an ice-cooled solution of (1R)-1,8,8-trimethylbicyclo [3.2.1]octane-2,4-dione (0.90 g, 5.0 mmole), triethylamine (0.50 g, 5.0 mmole) and 4-(dimethylamino)pyridine (0.61 g, 5.0 mmole) in dry dichloromethane (100 mL) was added a solution of 3,4-dichlorophenyl isocyanate (0.94 g, 10.0 mmole) in dry dichloromethane (25 mL). The resulting mixture was allowed to stir overnight under a nitrogen atmosphere, during which time it came up to room temperature, and then was heated at 30° C. for 24 hours. The reaction mixture was treated with 2N aqueous HCl and the layers separated. The acidic aqueous layer was extracted with two additional portions of dichloromethane. The combined organic layers were dried over anhydrous sodium sulfate and concentrated on a rotary evaporator to give a yellow oil, which was purified by chromatography on silica gel (10% ethyl acetate/hexane) to yield a yellow oil, which was crystallized from 95% ethanol to yield the title compound as a beige solid (1.07 g, 58% yield), mp=89–91° C.; MS (−) ESI m/z=366 (M−H)$^-$; $[\alpha]_D^{25}$=+25.9° (c=1, EtOH).

Analysis for $C_{18}H_{19}C_2NO_3$ Calculated: C: 58.71; H, 5.20; N, 3.80. Found: C: 59.46; H, 5.01; N, 3.70.

Example 15

(1R)-N-(4-nitrophenyl)-1,8,8-trimethyl-2,4-dioxobicyclo[3.2.1]octane-3-carboxamide To an ice-cooled solution of (1R)-1,8,8-trimethylbicyclo [3.2.1]octane-2,4-dione (0.36 g, 2.0 mmole), triethylamine (0.20 g, 2.0 mmole) and 4-(dimethylamino)pyridine (0.24 g, 2.0 mmole) in dry dichloromethane (25 mL) was added a solution of 4-nitrophenyl isocyanate (0.33 g, 2.0 mmole) in dry dichloromethane (5 mL). The resulting mixture was allowed to stir overnight under a nitrogen atmosphere, during which time it came up to room temperature, and then was heated at 30° C. for 24 hours. The reaction mixture was treated with 2N aqueous HCl and the layers separated. The acidic aqueous layer was extracted with two additional portions of dichloromethane. The combined organic layers were dried over anhydrous sodium sulfate and concentrated on a rotary evaporator to give a yellow oil, which was purified by chromatography on silica gel (10% ethyl acetate/ hexane) to yield an orange oil, which was crystallized from 95% ethanol to yield the title compound as an off-white solid (0.20 g, 30% yield), mp=168–170° C.; MS (−) ESI m/z=343 (M−H)$^-$; $[\alpha]_D^{25}$=+29.4° (c=1, DMSO).

Analysis for $C_{18}H_{20}N_2O_5$ Calculated: C: 62.78; H, 5.85; N, 8.13. Found: C: 62.58; H, 5.96; N, 7.76.

Example 16

(1R)-N-[4-chloro-3-(trifluoromethyl)phenyl]-1,8,8-trimethyl-2,4-dioxobicyclo [3.2.1]octane-3-carboxamide To an ice-cooled solution of (1R)-1,8,8-trimethylbicyclo [3.2.1]octane-2,4-dione (0.36 g, 2.0 mmole), triethylamine (0.20 g, 2.0 mmole) and 4-(dimethylamino)pyridine (0.24 g, 2.0 mmole) in dry dichloromethane (25 mL) was added a solution of 4-chloro-3-(trifluoromethyl)phenyl isocyanate (0.44 g, 2.0 mmole) in dry dichloromethane (5 mL). The resulting mixture was allowed to stir overnight under a nitrogen atmosphere, during which time it came up to room temperature, and then was heated at 30° C. for 7 hours. The reaction mixture was treated with 2N aqueous HCl and the layers separated. The acidic aqueous layer was extracted with two additional portions of dichloromethane. The combined organic layers were dried over anhydrous sodium sulfate and concentrated on a rotary evaporator to give a yellow oil, which was purified by chromatography on silica gel (10% ethyl acetate/hexane) to yield a yellow oil, which was crystallized from 95% ethanol to yield the title compound as a tan solid (0.36 g, 44% yield), mp=117–119° C.; MS (+) ESI m/z=402 (M+H)$^+$, $[\alpha]_D^{25}$=+22.3° (c=1, EtOH).

Analysis for $C_{18}H_{19}CF_3NO_3$ Calculated: C: 56.79; H, 4.77; N, 3.49. Found: C: 56.41; H, 4.72; N, 3.36.

Example 17

(1R)-N-[3-(trifluoromethyl)phenyl]-1,8,8-trimethyl-2,4-dioxobicyclo[3.2.1] octane-3-carboxamide To an ice-cooled solution of (1R)-1,8,8-trimethylbicyclo [3.2.1]octane-2,4-dione (0.36 g, 2.0 mmole), triethylamine (0.20 g, 2.0 mmole) and 4-(dimethylamino)pyridine (0.24 g, 2.0 mmole) in dry dichloromethane (25 mL) was added a solution of 3-(trifluoromethyl)phenyl isocyanate (0.37 g, 2.0 mmole) in dry dichloromethane (5 mL). The resulting mixture was allowed to stir overnight under a nitrogen atmosphere, during which time it came up to room temperature, and then was heated at 30° C. for 7 hours. The reaction mixture was treated with 2N aqueous HCl and the layers separated. The acidic aqueous layer was extracted with two additional portions of dichloromethane. The combined organic layers were dried over anhydrous sodium sulfate and concentrated on a rotary evaporator to give a yellow oil, which was purified by chromatography on silica gel (10% ethyl acetate/hexane) to yield a yellow oil, which was crystallized from 95% ethanol to yield the title compound as a beige solid (0.38 g, 51% yield), mp=66–68° C.; MS (–) ESI m/z=366 (M–H)$^-$; $[\alpha]_D^{25}$=+22.0° (c=1, EtOH).

Analysis for $C_{19}H_{20}F_3NO_3$ Calculated: C: 62.12; H, 5.49; N, 3.81. Found: C: 62.19; H, 5.46; N, 3.78.

Example 18

(1R)-N-[4-(trifluoromethyl)phenyl]-1,8,8-trimethyl-2,4-dioxobicyclo[3.2.1] octane-3-carboxamide To an ice-cooled solution of (1R)-1,8,8-trimethylbicyclo [3.2.1]octane-2,4-dione (0.36 g, 2.0 mmole), triethylamine (0.20 g, 2.0 mmole) and 4-(dimethylamino)pyridine (0.24 g, 2.0 mmole) in dry dichloromethane (20 mL) was added a solution of 4-(trifluoromethyl)phenyl isocyanate (0.41 g, 2.2 mmole) in dry dichloromethane (3 mL). The resulting reaction mixture was allowed to stir overnight under a nitrogen atmosphere, during which time it came up to room temperature. The resulting mixture was concentrated on a rotary evaporator and then partitioned between dichloromethane and 2N aqueous HCl. The organic layer was dried over anhydrous sodium sulfate and concentrated on a rotary evaporator to give a yellow oil, which was purified by chromatography on silica gel (15% ethyl acetate/hexane) to yield the title compound as a yellow solid (0.67 g, 91% yield), mp=78–81° C.; MS (–) ESI m/z=366 (M–H)$^-$; $[\alpha]$-D (25)=+24.2° (c=1, EtOH).

Analysis for $C_{19}H_{20}F_3NO_3$ Calculated: C: 62.12; H, 5.49; N, 3.81. Found: C: 62.21; H, 5.55; N, 3.37.

Example 19

(1R)-N-[4-chlorophenyl]-1,8,8-trimethyl-2,4-dioxobicyclo[3.2.1]octane-3-carboxamide To an ice-cooled solution of (1R)-1,8,8-trimethylbicyclo [3.2.1]octane-2,4-dione (0.36 g, 2.0 mmole), triethylamine (0.20 g, 2.0 mmole) and 4-(dimethylamino)pyridine (0.24 g, 2.0 mmole) in dry dichloromethane (25 mL) was added a solution of 4-chlorophenyl isocyanate (0.31 g, 2.0 mmole) in dry dichloromethane (5 mL). The resulting reaction mixture was allowed to stir overnight under a nitrogen atmosphere, during which time it came up to room temperature. It was then stirred at 30° C. for seven hours. The resulting mixture was treated with 2N aqueous HCl (30 mL) and the layers were separated. The aqueous layer was extracted with two additional portions of dichloromethane (50 mL). The combined organic layers were dried over anhydrous sodium sulfate and concentrated on a rotary evaporator. The desired product was isolated by chromatography on silica gel (10% ethyl acetate/hexane) and recrystallized from 95% ethanol to yield the title compound as a tan solid (0.39 g, 56% yield), mp=88–90° C.; MS (–) ESI m/z=334 (M+H)$^+$; $[\alpha]_D^{25}$=+22.8° (c=1, EtOH).

Analysis for $C_{18}H_{20}ClNO_3$ Calculated: C: 64.77; H, 6.04; N, 4.20. Found: C: 64.90; H, 6.03; N, 4.12.

Example 20

(1R)-N-[3-chloro-4-fluorophenyl]-1,8,8-trimethyl-2,4-dioxobicyclo[3.2.1] octane-3-carboxamide To an ice-cooled solution of (1R)-1,8,8-trimethylbicyclo [3.2.1]octane-2,4-dione (0.36 g, 2.0 mmole), triethylamine (0.20 g, 2.0 mmole) and 4-(dimethylamino)pyridine (0.24 g, 2.0 mmole) in dry dichloromethane (25 mL) was added a solution of 3-chloro-4-fluorophenyl isocyanate (0.34 g, 2.0 mmole) in dry dichloromethane (5 mL). The resulting reaction mixture was allowed to stir overnight under a nitrogen atmosphere, during which time it came up to room temperature. It was then stirred at 30° C. for seven hours. The resulting mixture was treated with 2N aqueous HCl (30 mL) and the layers were separated. The aqueous layer was extracted with two additional portions of dichloromethane (50 mL). The combined organic layers were dried over anhydrous sodium sulfate and concentrated on a rotary evaporator. The desired product was isolated by chromatography on silica gel (10% ethyl acetate/hexane) and recrystallized from 95% ethanol to yield the title compound as a light orange solid (0.39 g, 56% yield), mp=89–91° C.; MS (–) ESI m/z=352 (M–H)$^-$; $[\alpha]_D^{25}$=+24.0° (c=1, EtOH).

Analysis for $C_{18}H_{19}CFNO_3$ Calculated: C: 61.45; H, 5.44; N, 3.98. Found: C: 61.38; H, 5.37; N, 3.93.

Example 21

(1R)-N-[3(trifluoromethyl)-4-fluorophenyl]-1,8,8-trimethyl-2,4-dioxobicyclo [3.2.1]octane-3-carboxamide To an ice-cooled solution of (1R)-1,8,8-trimethylbicyclo [3.2.1]octane-2,4-dione (0.18 g, 1.0 mmole), triethylamine (0.10 g, 1.0 mmole) and 4-(dimethylamino)pyridine (0.12 g, 1.0 mmole) in dry dichloromethane (25 mL) was added a solution of 4-fluoro-3-(trifluoromethyl)phenyl isocyanate (0.21 g, 1.0 mmole) in dry dichloromethane (5 mL). The resulting reaction mixture was allowed to stir overnight under a nitrogen atmosphere, during which time it came up to room temperature. It was then stirred at 30° C. for twenty-four hours. The resulting mixture was treated with 2N aqueous HCl (30 mL) and the layers were separated. The aqueous layer was extracted with two additional portions of dichloromethane (50 mL). The combined organic layers were dried over anhydrous sodium sulfate and concentrated on a rotary evaporator. The desired product was isolated by chromatography on silica gel (10% ethyl acetate/hexane) and recrystallized from 95% ethanol to yield the title compound as a beige solid (0.18 g, 48% yield), mp=96–98° C.; MS (−) ESI m/z=384 (M−H)$^-$; $[\alpha]_D^{25}$=+22.1° (c=1, EtOH).

Analysis for $C_{19}H_{19}ClF_4NO_3$ Calculated: C: 59.22; H, 4.97; N, 3.63. Found: C 59.50; H, 5.01; N, 3.57.

Example 22

N-[3-(trifluoromethyl)phenyl]-2,4-dioxobicyclo [3.2.1]octane-3-carboxamide

A solution of bicyclo[3,2,1]octane-2,4-dione (0.27 g, 2.0 mmole), 3-(trifluoromethyl) phenyl isocyanate (0.55 ml, 4.0 mmole), and 60% sodium hydride in mineral oil (0.088 g, 2.2 mmole) in dimethylformamide (100 mL) was stirred at 0° C. for 1 hour and then heated at 45–50° C. under nitrogen for 24 hours. After cooling, the mixture was diluted with $H_2O$ and treated with 2N aqueous HCl until the mixture was clear. The clear solution was then extracted with dichloromethane. The organic layer was washed with $H_2O$ again, dried over anhydrous magnesium sulfate, and concentrated on a rotary evaporator. The residue was purified with by chromatography on silica gel (40% dichloromethane/hexane) to give a clear oily liquid as the expected product. The oily product was crystallized with ethyl acetate/hexane in a dry ice bath to afford the title compound as a white solid, mp=68–69° C.; MS (−) ESI m/z=324 (M−H)$^-$.

Analysis for $C_{16}H_{14}F_3NO_3$ Calculated: C: 59.08; H, 4.34; N, 4.20. Found: C: 59.04; H, 4.20; N, 4.30.

Example 23

N-[3,5-bis(trifluoromethyl)phenyl]-2,4-dioxobicyclo [3.2.1]octane-3-carboxamide

A solution of bicyclo[3,2,1]octane-2,4-dione (0.34 g, 2.5 mmole), 3,5-bis(trifluoromethyl)phenyl isocyanate (0.86 ml, 5.0 mmole), and 60% sodium hydride in mineral oil (0.11 g, 2.75 mmole) in dimethylformamide (100 mL) was stirred at 0° C. for 1 hour and heated at 45–50° C. under nitrogen for 24 hours. After cooling, the mixture was diluted with $H_2O$ and treated with 2N aqueous HCl until the mixture was clear. The clear solution was then extracted with dichloromethane. The organic layer was washed with $H_2O$ again, dried over anhydrous magnesium sulfate, and concentrated on a rotary evaporator. The residue was purified by chromatography on silica gel (30% dichloromethane/hexane) to give a clear oil as the expected product. The oily product was crystallized by triturated with hexane in a dry ice bath and collected at room temperature to give the title compound as a white solid, mp=88–90° C.; (−) ESI m/z=392 (M−H)$^-$.

Analysis for $C_{17}H_{13}F_6NO_3$ Calculated: C: 51.92; H, 3.33; N, 3.56. Found: C: 51.74; H, 3.38; N, 3.47.

Example 24

N-([3,4-dichlorophenyl)-2,4-dioxobicyclo[3.2.1] octane-3-carboxamide

A solution of bicyclo[3,2,1]octane-2,4-dione (0.34 g, 2.5 mmole), 3,4-dichlorophenyl isocyanate (0.94 g, 5 mmole), and 60% sodium hydride in mineral oil (0.11 g, 2.75 mmole) in dimethylformamide (100 mL) was stirred at 0° C. for 1 hour and heated at 45–50° C. under nitrogen for 24 hours. After cooling, the mixture was diluted with $H_2O$ and treated with 2N aqueous HCl until the mixture was clear. The clear solution was then extracted with dichloromethane. The organic layer was washed with $H_2O$ again, dried over anhydrous magnesium sulfate, and concentrated on a rotary evaporator. The residue was purified by chromatography on silica gel (40% dichloromethane/hexane) to give an oily solid as the expected product. The oily product was recrystallized from ethyl acetate/hexane to afford the title compound as a white solid, mp=146–148° C.; MS (−) ESI m/z=325 (M−H)$^-$.

Analysis for $C_{15}H_{13}Cl_2NO_3$ Calculated: C: 55.24; H, 4.02; N, 4.29. Found: C: 55.11; H, 3.97; N, 4.21.

Example 25

N-[4-chloro-3-(trifluoromethyl)phenyl]-2,4-dioxobicyclo[3.2.1]octane-3-carboxamide A solution of bicyclo[3,2,1]octane-2,4-dione (0.552 g, 4.0 mmole), 4-chloro-3-(trifluoromethyl)phenyl isocyanate (1.77 g, 8.0 mmole), and 60% sodium hydride in mineral oil (0.176 g, 4.4 mmole) in dimethylformamide (150 mL) was stirred at 0° C. for 1 hour and heated at 45–50° C. under nitrogen for 24 hours. After cooling, the mixture was diluted with $H_2O$ and treated with 2N HCl until the mixture was clear. The clear solution was then extracted with dichloromethane. The organic layer was washed with $H_2O$ again, dried over anhydrous magnesium sulfate, and concentrated on a rotary evaporator. The residue was purified by chromatography on silica gel (30% dichloromethane/hexane) to give a clear oil as the expected product. The oily product was crystallized with ethyl acetate/hexane in a dry ice bath to afford the title compound as a white solid, mp=136–137° C.; MS (−) ESI m/z=358 (M−H)$^-$. Analysis for $C_{16}H_{13}ClF_3NO_3$ Calculated: C: 53.42; H, 3.64; N, 3.89. Found: C: 53.37; H, 3.57; N, 3.67.

Example 26

N-[4-(trifluoromethyl)phenyl]-2,4-dioxobicyclo [3.2.1]octane-3-carboxamide

To a solution of bicyclo[3,2,1]octane-2,4-dione (0.28 g, 2.0 mmole) in anhydrous tetrahydrofuran (8 mL) was added, under a nitrogen atmosphere, sodium metal (0.05 g, 2.0 mmole). The resulting mixture was stirred under nitrogen for 48 hours, during which time a white precipitate formed. The white precipitate was collected by vacuum filtration, washed with cold tetrahydrofuran, and dried in vacuo. It was then resuspended in anhydrous tetrahydrofuran (8 mL) and a solution of 3-(trifluoromethyl)phenyl isocyanate (0.44 g, 2.35 mmole) in anhydrous tetrahydrofuran (7 mL) was added dropwise. The resulting mixture was refluxed for 4 hours under a nitrogen atmosphere, cooled to room temperature, and concentrated on a rotary evaporator. The oily residue was triturated with diethyl ether and the resulting white precipitate was collected by vacuum filtration and washed with diethyl ether to yield the sodium salt of the title compound (0.18 g, 26% yield), mp=250–260° C.; MS (−) ESI m/z=324 (M−H)−.

Analysis for $C_{16}H_{13}F_3NO_3 \cdot Na \cdot 0.5H_2O$ Calculated: C: 53.94; H, 3.96; N, 3.93. Found: C: 53.88; H, 4.14; N, 4.04.

Example 27

N-[4-fluoro-3-(trifluoromethyl)phenyl]-2,4-dioxobicyclo[3.2.1]octane-3-carboxamide Sodium hydride (60% dispersion in mineral oil, 0.064 g, 1.59 mmol) was washed with dry hexane under a nitrogen atmosphere to remove mineral oil. It was then suspended in dry tetrahydrofuran (3 mL). To the suspension was added a solution of 2,4-dioxobicyclo[3.2.1]octane (0.20 g, 1.45 mmol) in dry tetrahydrofuran (10 mL). The resulting mixture was stirred at room temperature under a nitrogen atmosphere overnight. It was then treated with 4-fluoro-3-(trifluoromethyl)phenyl isocynate (0.31 mL, 2.17 mmol) via syringe. The resulting mixture was stirred at room temperature under a nitrogen atmosphere overnight. The reaction mixture was then concentrated on a rotary evaporator and the residue was partitioned between dichloromethane (150 mL) and 1N aqueous HCl (100 mL). The aqueous layer was extracted twice with additional portions of dichloromethane ((25 mL). The combined organic layers were dried over anhydrous sodium sulfate and concentrated on a rotary evaporator. The desired product was isolated by chromatography on silica gel (2% methanol/dichloromethane) to yield the title compound as a light yellow solid (0.36 g, 73% yield), mp=97–100° C.; MS (−) ESI m/z=342 (M−H)−.

Analysis for $C_{16}H_{13}F_4NO_3$ Calculated: C: 55.98; H, 3.82; N, 4.08. Found: C: 55.63; H, 3.40; N, 4.43.

Example 28

6,6-Dimethyl-2,4-dioxo-N-[4-(trifluoromethyl)phenyl]bicyclo[3.1.1]heptane-3-carboxamide To a solution of 6,6-dimethylbicyclo[3.1.1]heptane-2,4-dione (Intermediate I, 0.25 g, 1.64 mmol) in dry tetrahydrofuran (40 mL) under a nitrogen atmosphere was added sodium hydride (60% dispersion in mineral oil, 0.074 g, 1.81 mmol) at room temperature. The mixture was stirred for 30 minutes and then ααα-trifluoro-p-tolylisocyanate (0.26 ml, 1.81 mmol) was added via syringe. The reaction was stirred overnight under nitrogen at room temperature and then quenched with water (5 mL). Tetrahydrofuran was removed on a rotary evaporator and additional water (30 mL) was added. The aqueous mixture was extracted with ethyl acetate (3×70 mL). The combined organic layers were washed with brine (10 mL), dried over anhydrous sodium sulfate, and concentrated on a rotary evaporator to give a yellow solid, which was triturated with diethyl ether (2×5 mL) under sonication to provide the sodium salt of the desired product as a light yellow solid (0.46 g; 78% yield), mp>230° C.; MS (−) ESI m/z=338 (M−H)−.

Analysis for $C_{17}H_{15}F_3NO_3 \cdot Na \cdot 0.2H_2O$ Calculated: C: 55.96; H, 4.25; N, 3.84. Observed: C: 55.98; H, 4.19; N, 3.75.

Example 29

6,6-Dimethyl-2,4-dioxo-N-[3-(trifluoromethyl)phenyl]bicyclo[3.1.1]heptane-3-carboxamide To a solution of 6,6-dimethylbicyclo[3.1.1]heptane-2,4-dione (Intermediate I, 0.21 g, 1.38 mmol) in dry tetrahydrofuran (40 mL) under a nitrogen atmosphere was added sodium hydride (60% dispersion in mineral oil, 0.055 g, 1.38 mmol) at room temperature. The mixture was stirred for 30 minutes and then ααα-trifluoro-m-tolylisocyanate (0.19 ml, 1.38 mmol) was added via syringe. The reaction was stirred overnight under nitrogen at room temperature and then quenched with water (5 mL). Tetrahydrofuran was removed on a rotary evaporator and additional water (30 mL) was added. The aqueous mixture was extracted with ethyl acetate (3×70 mL). The combined organic layers were washed with brine (10 mL), dried over anhydrous sodium sulfate, and concentrated on a rotary evaporator to give a yellow solid, which was triturated with diethyl ether (2×5 mL) under sonication to provide the sodium salt of the desired product as a light yellow solid (0.34 g; 73% yield), mp>230° C.; MS (−) ESI m/z=338 (M−H)−.

Analysis for $C_{17}H_{15}F_3NO_3 \cdot Na \cdot 0.2H_2O$ Calculated: C: 55.96; H, 4.25; N, 3.84. Observed: C: 55.99; H, 4.27; N, 3.67.

Example 30

6,6-Dimethyl-2,4-dioxo-N-(3-chloro-4-fluorophenyl)bicyclo[3.1.1]heptane-3-carboxamide To a solution of 6,6-dimethylbicyclo[3.1.1]heptane-2,4-dione (Intermediate I, 0.235 g, 1.54 mmol) in dry tetrahydrofuran (40 mL) under a nitrogen atmosphere was added sodium hydride (60% dispersion in mineral oil, 0.062 g, 1.54 mmol) at room temperature. The mixture was stirred for 30 minutes and then 3-chloro-4-fluorophenylisocyanate (0.19 ml, 1.54 mmol) was added via syringe. The reaction was stirred overnight under nitrogen at room temperature and then quenched with water (5 mL). Tetrahydrofuran was removed on a rotary evaporator and additional water (30 mL) was added. The aqueous mixture was extracted with ethyl acetate (3×70 mL). The combined organic layers were washed with brine (10 mL), dried over anhydrous sodium sulfate, and concentrated on a rotary evaporator to give a yellow solid, which was triturated with diethyl ether (2×5 mL) under sonication to provide the sodium salt of the desired product as a light yellow solid (0.37 g; 73% yield), mp>230° C.; MS (−) ESI m/z=322 (M−H)−.

Analysis for $C_{16}H_{14}ClFNO_3$ Na Calculated: C: 55.59; H, 4.08; N, 4.05. Observed: C: 55.25; H, 4.26; N, 3.90.

Example 31

6,6-Dimethyl-2,4-dioxo-N-[4-fluoro-3 (trifluoromethyl)phenyl]bicyclo[3.1.1]heptane-3-carboxamide To a solution of 6,6-dimethylbicyclo[3.1.1]heptane-2,4-dione (Intermediate I, 0.25 g, 1.64 mmol) in dry tetrahydrofuran (30 mL) under a nitrogen atmosphere was added sodium hydride (60% dispersion in mineral oil, 0.072 g, 1.80 mmol) at room temperature. The mixture was stirred for 30 minutes and then 4-fluoro-3-(trifluoromethyl)phenylisocyanate (0.26 ml, 1.80 mmol) was added via syringe. The reaction was stirred overnight under nitrogen at room temperature and then quenched with water (5 mL). Tetrahydrofuran was removed on a rotary evaporator and additional water (30 mL) was added. The aqueous mixture was extracted with ethyl acetate (3×70 mL). The combined organic layers were washed with brine (10 mL), dried over anhydrous sodium sulfate, and concentrated on a rotary evaporator to give a yellow solid, which was triturated with diethyl ether (5 mL) under sonication and washed with ethyl acetate (3 mL) to provide the sodium salt of the desired product as a white solid (0.30 g; 49% yield), mp>230° C.; MS (−) ESI m/z=356 (M−H)⁻.

Analysis for $C_{17}H_{14}F_4NO_3$ Na 0.2H$_2$O Calculated: C: 53.33; H, 3.79; N, 3.66. Observed: C: 53.19; H, 3.68; N, 3.55.

Example 32

6,6-Dimethyl-2,4-dioxo-N-(3,4-dichlorophenyl)bicyclo[3.1.1]heptane-3-carboxamide To a solution of 6,6-dimethylbicyclo[3.1.1]heptane-2,4-dione (Intermediate I, 0.25 g, 1.64 mmol) in dry tetrahydrofuran (30 mL) under a nitrogen atmosphere was added sodium hydride (60% dispersion in mineral oil, 0.072 mg, 1.80 mmol) at room temperature. The mixture was stirred for 30 minutes and then 3,4-dichlorophenylisocyanate (0.34 g, 1.80 mmol) was added. The reaction was stirred overnight under nitrogen at room temperature and then quenched with water (5 mL). Tetrahydrofuran was removed on a rotary evaporator and additional water (30 mL) was added. The aqueous mixture was extracted with ethyl acetate (3×70 mL). The combined organic layers were washed with brine (10 mL), dried over anhydrous sodium sulfate, and concentrated on a rotary evaporator to give a yellow solid, which was triturated with diethyl ether (5 mL) under sonication and washed with ethyl acetate (3 mL) to provide the sodium salt of the desired product as a white solid (0.37 g; 62% yield), mp>230° C.; MS (−) ESI m/z=338 (M−H)⁻.

Analysis for $C_{16}H_{14}Cl_2NO_3$ Na 0.2H$_2$O Calculated: C: 52.54; H, 3.97; N, 3.83. Observed: C: 52.29; H, 3.89; N, 3.68.

Example 33

6,6-Dimethyl-2,4-dioxo-N-(3,5-dichlorophenyl)bicyclo[3.1.1]heptane-3-carboxamide To a solution of 6,6-dimethylbicyclo[3.1.1]heptane-2,4-dione (Intermediate I, 0.22 g, 1.45 mmol) in dry tetrahydrofuran (30 mL) under a nitrogen atmosphere was added sodium hydride (60% dispersion in mineral oil, 0.064 g, 1.59 mmol) at room temperature. The mixture was stirred for 30 minutes and then 3,5-dichlorophenylisocyanate (0.22 ml, 1.59 mmol) was added via syringe. The reaction was stirred overnight under nitrogen at room temperature and then quenched with water (5 mL). Tetrahydrofuran was removed on a rotary evaporator and additional water (30 mL) was added. The aqueous mixture was extracted with ethyl acetate (3×70 mL). The combined organic layers were washed with brine (10 mL), dried over anhydrous sodium sulfate, and concentrated on a rotary evaporator to give a yellow solid, which was recrystallized from tetrahydrofuran/diethyl ether to provide the sodium salt of the desired product as a white solid (0.32 g; 61% yield), mp>230° C.; MS (−) ESI m/z=338 (M−H)⁻.

Analysis for $C_{16}H_{14}Cl_2NO_3$ Na 0.2H$_2$O Calculated: C: 52.54; H, 3.97; N, 3.83. Observed: C: 52.59; H, 3.99; N, 3.68.

Example 34

6,6-Dimethyl-2,4-dioxo-N-(4-fluorophenyl)bicyclo[3.1.1]heptane-3-carboxamide

To a solution of 6,6-dimethylbicyclo[3.1.1]heptane-2,4-dione (Intermediate I, 0.22 g, 1.45 mmol) in dry tetrahydrofuran (30 mL) under a nitrogen atmosphere was added sodium hydride (60% dispersion in mineral oil, 0.064 g, 1.59 mmol) at room temperature. The mixture was stirred for 30 minutes and then 4-fluorophenyl isocyanate (0.18 ml, 1.59 mmol) was added via syringe. The reaction was stirred overnight under nitrogen at room temperature and then quenched with water (5 mL). Tetrahydrofuran was removed on a rotary evaporator and additional water (30 mL) was added. The aqueous mixture was extracted with ethyl acetate (3×70 mL). The combined organic layers were washed with brine (10 mL), dried over anhydrous sodium sulfate, and concentrated on a rotary evaporator to give the crude product, which was recrystallized from tetrahydrofuran to provide the sodium salt of the desired product as a white solid (0.33 g; 73% yield), mp>230° C.; MS (−) ESI m/z=288 (M−H)⁻.

Analysis for $C_{16}H_{15}FNO_3$ Na 0.2H$_2$O Calculated: C: 61.03; H, 4.93; N, 4.45. Observed: C: 60.86; H, 4.85; N, 4.33.

Example 35

6,6-Dimethyl-2,4-dioxo-N-(3-chlorophenyl)bicyclo[3.1.1]heptane-3-carboxamide

To a solution of 6,6-dimethylbicyclo[3.1.1]heptane-2,4-dione (Intermediate I, 0.22 g, 1.45 mmol) in dry tetrahydrofuran (30 mL) under a nitrogen atmosphere was added sodium hydride (60% dispersion in mineral oil, 0.064 g, 1.59 mmol) at room temperature. The mixture was stirred for 30 minutes and then 3-chlorophenyl isocyanate (0.19 ml, 1.59 mmol) was added via syringe. The reaction was stirred overnight under nitrogen at room temperature and then quenched with water (5 mL). Tetrahydrofuran was removed on a rotary evaporator and additional water (30 mL) was added. The aqueous mixture was extracted with ethyl acetate (3×70 mL). The combined organic layers were washed with brine (10 mL), dried over anhydrous sodium sulfate, and concentrated on a rotary evaporator to give a yellow solid, which was triturated with diethyl ether (2×5 mL) under sonication to provide the sodium salt of the desired product as a light yellow solid (0.24 g; 51% yield), mp>230° C.; MS (−) ESI m/z=304 (M−H)⁻.

Analysis for $C_{16}H_{15}ClNO_3$ Na $0.8H_2O$ Calculated: C: 56.17; H, 4.89; N, 4.45. Observed: C: 56.18; H, 4.61; N, 4.00.

Example 36

6,6-Dimethyl-2,4-dioxo-N-(4-chlorophenyl)bicyclo[3.1.1]heptane-3-carboxamide

To a solution of 6,6-dimethylbicyclo[3.1.1]heptane-2,4-dione (Intermediate I, 0.22 g, 1.45 mmol) in dry tetrahydrofuran (30 mL) under a nitrogen atmosphere was added sodium hydride (60% dispersion in mineral oil, 0.064 g, 1.59 mmol) at room temperature. The mixture was stirred for 30 minutes and then 4-chlorophenyl isocyanate (0.20 ml, 1.59 mmol) was added via syringe. The reaction was stirred overnight under nitrogen at room temperature and then quenched with water (5 mL). Tetrahydrofuran was removed on a rotary evaporator and additional water (30 mL) was added. The aqueous mixture was extracted with ethyl acetate (3×70 mL). The combined organic layers were washed with brine (10 mL), dried over anhydrous sodium sulfate, and concentrated on a rotary evaporator to give a yellow oil, which crystallized from tetrahydrofuran/diethyl ether to provide the sodium salt of the desired product as a white solid (0.33 g; 74% yield), mp>230° C.; MS (−) ESI m/z=304 (M−H)⁻.

Analysis for $C_{16}H_{15}ClNO_3$ Na Calculated: C: 58.64; H, 4.61; N, 4.27. Observed: C: 56.40; H, 4.58; N, 4.18.

Example 37

N-[3,5-bis(trifluoromethyl)phenyl]-2,4-dioxobicyclo[3.2.2]nonane-3-carboxamide

Into an oven-dried 25 mL three-neck round bottom flask under a nitrogen atmosphere was placed sodium hydride (0.06 g, 1.50 mmol, 60% suspension in mineral oil). The mineral oil was removed by washing with dry hexane and the resulting material was suspended in dry tetrahydrofuran (3 mL). To the stirred suspension was added a solution of Intermediate II (0.20 g, 1.32 mmol) in dry tetrahydrofuran (10 mL). The resulting mixture was stirred at room temperature under nitrogen overnight (16 hr) and then warmed at 60° C. for 1 hour. To the cooled reaction mixture was then added 3,5-bis(trifluoromethyl)phenylisocyanate (0.46 mL, 2.64 mmol) via syringe. The resulting mixture was stirred at room temperature under nitrogen for 3 days. The tetrahydrofuran was removed on a rotary evaporator and the residue was partitioned between dichloromethane (100 mL) and 1N aqueous HCl (100 mL). The aqueous layer was extracted with two additional portions (25 mL) of dichloromethane, and the combined organic layers were dried over anhydrous sodium sulfate and concentrated on a rotary evaporator. The desired product was isolated by chromatography on silica gel (25% hexane/dichloromethane). It was converted to its sodium salt in methanol by treatment with one equivalent of sodium methoxide in methanol and recrystallized from diethyl ether/hexane to afford the desired product as a white solid (0.40 g, 73%), mp=286–288° C.; MS (−) ESI m/z=406 (M−H)⁻.

Analysis for $C_{18}H_{15}F_6NO_3$·Na. $1.0H_2O$ Calculated: C: 48.33; H, 3.61; N, 3.13. Found: C: 48.01; H, 3.51; N, 3.05.

Example 38

Xenopus Oocytes Current Assay

The compounds of formula I were examined for their ability to inhibit the inactivation of the human Kv1.1/Kvβ1 potassium ion channel complex in vitro using electrophysiological current recordings on inactivating Kv1.1/Kvβ1 channels expressed in *Xenopus* oocytes. *Xenopus* oocytes were harvested from frogs under general anesthesia using aseptic techniques. Oocytes were treated with 2 mg/ml collagenase for 1–1.5 hr, defolliculated, and injected with 40 nL cRNA (a mixture of hky1.1 and hKvβ1) produced using standard molecular biological techniques (Sambrook, et al., 1989, *Molecular Cloning: A Laboratory Manual*). The concentration of hKv1.1/hKvp1 cRNA varies, but was generally about 50 ng/μL hKv1.1 and 0.5–1.5 mg/μL hKβ1.

Currents were recorded using standard voltage clamp amplifiers at room temperature. Recordings were performed in the bath solution "ND-96" containing 96 mM NaCl, 2 mM KCl, 1 mm $CaCl_2$, 1 mM $MgCl_2$, 10 mM HEPES and 50 mg/μL Gentamycin (pH=7.6). The pipette (electrode) solution generally consisted of 3 mM KCl. Electrodes were made from WPI TW150F-4 borosilicate glass (or equivalent) and typically had resistances of 0.5–1.5 Mohms. The standard current-voltage (IV) pulse protocol consisted of voltage steps from −60 mV to +50 mV, in 10 mV increments for 200 ms, at a frequency of one IV set per 2 minutes. Data were digitized and analyzed by standard software packages.

Solutions of the test compounds consisting of test compounds dissolved in bath solution were applied by bath perfusion using gravity or pump-driven flow. A minimum of 2 mL (10 times the bath volume) over 3 minutes were flowed for each compound concentration tested. Data were averaged across at least 3 cells tested for each concentration.

Test compounds were examined for their ability to inhibit the inactivation of the steady state portion of the IV curve. Results are presented as a percent increase in the steady state current relative to control experiments in which oocytes were treated with bath solution which did not contain test compound. The compounds of this invention displayed the ability to inhibit the inactivation of the steady state current an Kv1.1/Kvβ1 potassium ion channel complex, as measured by the steady state current versus control (Table 1).

TABLE 1

| Example | Percent Increase in Steady State Current Of human Kv1.1/Kvβ1 @ a concentration of 50 μM |
|---|---|
| 1 | 16% |
| 2 | 22% |
| 4 | 11% |
| 8 | 53% |
| 9 | 27% |
| 10 | 137% |
| 12 | 22% |
| 13 | 19% |
| 15 | 75% |
| 16 | 45% |
| 18 | 96% |
| 19 | 14% |
| 20 | 267% |
| 21 | 229% |
| 22 | 41% |
| 23 | 137% |
| 24 | 28% |
| 25 | 47% |
| 27 | 43% |
| 28 | 190% |

TABLE 1-continued

| Example | Percent Increase in Steady State Current Of human Kvβ1.1/Kvβ1 @ a concentration of 50 μM |
|---|---|
| 29 | 67% |
| 30 | 124% |
| 31 | 282% |
| 32 | 311% |
| 33 | 326% |
| 34 | 94% |
| 35 | 107% |
| 36 | 125% |
| 37 | 68% |

The compounds of formula I were also examined for their anticonvulsant activity in vivo by assessing their ability to inhibit the seizures induced by administration of pentylenetetrazole (PTZ). Adult mice were pretreated intraperitoneally with the test compound. Thirty minutes later these animals were challenged with pentylenetetrazole (85 mg/kg, s.c.) and observed for onset of seizures during a 30 minute test period. Compounds of formula I inhibited the convulsions induced by treatment with PTZ. ED50 values for the compounds of Examples 1 to 37 which were tested varied, but generally fell within the dose range of 10–100 mg/kg i.p.

Example 39

Anxiolytic Activity

Anxiolytic activity of the compounds of formula I was determined using the mouse Elevated Zero Maze model, originally described by Shepherd, et al. (Psychopharmocol. (1994) 116:56–64), incorporated herein by reference in its entirety. Anxiolytic efficacy was measured as the ability of the test compound to increase the amount of time that the mice spent in the open zones of the maze. To account for the possibility of false positive results due to increased locomotor activity, total distance traveled during the course of the experiment was also monitored.

The compound of Example 2 ((1S)-N-[3-(trifluoromethyl)phenyl]-1,8,8-trimethyl-2,4-dioxobicyclo[3.2.1]octane-3-carboxamide) was examined in the Elevated Zero Maze model and compared with the known anxiolytic diazepam. As can be seen from the data in Table 2, the compound of Example 2, when administered at a dose of 60 mg/kg ip., increased the amount of time that the test animals spent in the open zones of the maze by 140%. Diazepam evoked a similar response at therapeutically relevant doses. Treatment with diazepam resulted in a small decrease in the total distance traveled, while there was no significant change in the total distance traveled in the presence of the compound of Example 2.

TABLE 2

| Compound/Dose | % Time Spent in Open Zones (Relative to Control) | % Total Distance Traveled (Relative to Control) |
|---|---|---|
| Diazepam (3 mg/kg ip.) | 220% | 75% |
| Example 2 (60 mg/kg ip.) | 140% | 102% |

Experimental Protocol for Elevated Zero Maze

The zero maze, constructed of black Perspex, consisted of a circle (outer diameter approximately 60 cm, width 5 cm) that was elevated 55 cm above the floor. The zero maze was divided into 4 equal quadrants, alternating between open and closed. The closed quadrants had walls extending 20 cm above the surface of the maze and the open quadrants had a lip, constructed of clear perspex, extending 3 mm above the surface of the maze. Animals were tested under low levels of illumination in the presence of red light. Test animals (male CN57BI/n mice) were group housed with ad lib access to food and water. On the day of testing, animals were brought into the behavioral testing room and allowed to habituate for a period of not less than one-half hour. Test compounds were administered at the appropriate dose ip. 30 min prior to testing on the zero maze. Control animals were administered the test vehicle. Animals were placed on the zero maze with their head and forepaws contained within a closed quadrant. The animals' behavior was then recorded for 4 minutes and the distance traveled, the amount of time spent in, and number of entries into, each quadrant was noted. Behavior was monitored utilizing an automated video tracking system. Results for the test compounds are presented here as the percentage relative to that obtained with the control animals.

The entire disclosure of each patent, patent application, and publication cited or described in this document is hereby incorporated by reference.

What is claimed is:

1. A compound having formula (I):

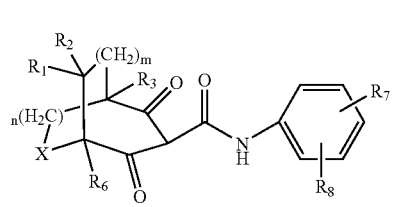

or a tautomer thereof, or a pharmaceutically acceptable salt thereof or both, wherein:

X is a bond or $CR_4R_5$;

$R_1$, $R_2$, $R_4$, and $R_5$ are, independently, hydrogen or a $C_1$ to $C_6$ alkyl;

$R_3$ and $R_6$ are, independently hydrogen or a $C_1$ to $C_6$ alkyl;

$R_7$ and $R_8$ are, independently, hydrogen, a halogen atom, a hydroxyl group, a $C_1$ to $C_6$ alkyl, a $C_1$ to $C_6$ alkoxy, a $C_1$ to $C_4$ perhalogenated alkyl, a $C_1$ to $C_4$ perhalogenated alkoxy, a $C_2$ to $C_7$ alkenyl, CN, $NO_2$, $CO_2R_9$, $COR_9$, alkanesulfonyl, or $NR_9R_{10}$;

m and n are, independently, 0 or 1; and $R_9$ and $R_{10}$ are, independently, hydrogen or a $C_1$ to $C_6$ alkyl.

2. A compound of claim 1 wherein X is $CR_4R_5$, and $R_1$, $R_2$, $R_4$, and $R_5$ are, independently, H or methyl.

3. A compound of claim 2 wherein $R_1$ and $R_2$ are each methyl, or $R_4$ and $R_5$ are each methyl.

4. A compound of claim 1 wherein X is $CR_4R_5$, and $R_1$, $R_2$, $R_4$, and $R_5$ are each H.

5. A compound of claim 1 wherein $R_3$ and $R_6$ are, independently, H or methyl.

6. A compound of claim 1 wherein X is $CR_4R_5$, m is 0 and n is 1.

7. A compound of claim 6 wherein $R_1$ and $R_2$ are each methyl, $R_4$ and $R_5$ are each H, and $R_3$ and $R_6$ are H or methyl.

8. A compound of claim 7 wherein $R_7$ and $R_8$ are, independently, H, $C_1$ to $C_6$ alkyl, halogen, nitro, $C_1$ to $C_6$ dialkylamino, or $C_1$ to $C_4$ perhalogenated alkyl.

9. A compound of claim 6 wherein $R_1$ and $R_2$ are each H, $R_4$ and $R_5$ are each H, and $R_3$ and $R_6$ are H or methyl.

10. A compound of claim 9 wherein $R_7$ and $R_8$ are, independently, H, $C_1$ to $C_6$ alkyl, halogen, nitro, $C_1$ to $C_6$ dialkylamino, or $C_1$ to $C_4$ perhalogenated alkyl.

11. A compound of claim 1 wherein m and n are each 0.

12. A compound of claim 11 wherein X is $CR_4R_5$; $R_1$, $R_2$, $R_4$, and $R_5$ are, independently, H or methyl; and $R_3$ and $R_6$ are each H.

13. A compound of claim 12 wherein $R_7$ and $R_8$ are, independently, H, $C_1$ to $C_6$ alkyl, halogen, nitro, $C_1$ to $C_6$ dialkylamino, or $C_1$ to $C_4$ perhalogenated alkyl.

14. A compound of claim 11 wherein X is $CR_4R_5$; $R_1$ and $R_2$ are each H; $R_4$ and $R_5$ are each methyl, and $R_3$ and $R_6$ are each H.

15. A compound of claim 14 wherein $R_7$ and $R_8$ are, independently, H, $C_1$ to $C_6$ alkyl, halogen, nitro, $C_1$ to $C_6$ dialkylamino, or $C_1$ to $C_4$ perhalogenated alkyl.

16. A compound of claim 1 wherein m and n are each 1.

17. A compound of claim 16 wherein X is $CR_4R_5$; $R_1$ and $R_2$ are each H; $R_4$ and $R_5$ are each H, and $R_3$ and $R_6$ are each H or methyl.

18. A compound of claim 17 wherein $R_7$ and $R_8$ are, independently, H, $C_1$ to $C_6$ alkyl, halogen, nitro, $C_1$ to $C_6$ dialkylamino, or $C_1$ to $C_4$ perhalogenated alkyl.

19. A compound of claim 1 wherein $R_7$ and $R_8$ are, independently, H, $C_1$ to $C_6$ alkyl, halogen, nitro, $C_1$ to $C_6$ dialkylamino, or $C_1$ to $C_4$ perhalogenated alkyl.

20. A compound of claim 19 wherein $R_7$ and $R_8$ are, independently, H, methyl, chlorine, fluorine, nitro, dimethylamino, or perfluoromethyl.

21. A compound of claim 1 selected from the group consisting of:
- N-[3,5-bis(trifluoromethyl)phenyl]-1,8,8-trimethyl-2,4-dioxobicyclo[3.2.1]octane-3-carboxamide;
- N-[3-(trifluoromethyl)phenyl]-1,8,8-trimethyl-2,4-dioxobicyclo[3.2.1]octane-3-carboxamide;
- N-(3,5-dichlorophenyl)-1,8,8-trimethyl-2,4-dioxobicyclo[3.2.1]octane-3-carboxamide;
- N-(3,4-dichlorophenyl)-1,8,8-trimethyl-2,4-dioxobicyclo[3.2.1]octane-3-carboxamide;
- N-(3-nitrophenyl)-1,8,8-trimethyl-2,4-dioxobicyclo[3.2.1]octane-3-carboxamide;
- N-(4-nitrophenyl)-1,8,8-trimethyl-2,4-dioxobicyclo[3.2.1]octane-3-carboxamide;
- N-[4-chloro-3-(trifluoromethyl)phenyl]-1,8,8-trimethyl-2,4-dioxobicyclo[3.2.1]octane-3-carboxamide;
- N-[4-(trifluoromethyl)phenyl]-1,8,8-trimethyl-2,4-dioxobicyclo[3.2.1]octane-3-carboxamide;
- N-[4-(dimethylamino)phenyl]-1,8,8-trimethyl-2,4-dioxobicyclo[3.2.1]octane-3-carboxamide;
- N-[3-chloro-4-fluorophenyl]-1,8,8-trimethyl-2,4-dioxobicyclo[3.2.1]octane-3-carboxamide;
- N-[4-methylphenyl]-1,8,8-trimethyl-2,4-dioxobicyclo[3.2.1]octane-3-carboxamide;
- N-[4-fluoro-3-(trifluoromethyl)phenyl]-1,8,8-trimethyl-2,4-dioxobicyclo[3.2.1]octane-3-carboxamide;
- N-[4-chlorophenyl]-1,8,8-trimethyl-2,4-dioxobicyclo[3.2.1]octane-3-carboxamide;
- N-[3-(trifluoromethyl)phenyl]-2,4-dioxobicyclo[3.2.1]octane-3-carboxamide;
- N-[3,5-bis(trifluoromethyl)phenyl]-2,4-dioxobicyclo[3.2.1]octane-3-carboxamide;
- N-([3,4-dichlorophenyl)-2,4-dioxobicyclo[3.2.1]octane-3-carboxamide;
- N-[4-chloro-3-(trifluoromethyl)phenyl]-2,4-dioxobicyclo[3.2.1]octane-3-carboxamide;
- N-[4-(trifluoromethyl)phenyl]-2,4-dioxobicyclo[3.2.1]octane-3-carboxamide;
- N-[4-fluoro-3-(trifluoromethyl)phenyl]-2,4-dioxobicyclo[3.2.1]octane-3-carboxamide;
- 6,6-Dimethyl-2,4-dioxo-N-[4-(trfluoromethyl)phenyl]bicyclo[3.1.1]heptane-3-carboxamide;
- 6,6-Dimethyl-2,4-dioxo-N-[3-(trifluoromethyl)phenyl]bicyclo[3.1.1]heptane-3-carboxamide;
- 6,6-Dimethyl-2,4-dioxo-N-(3-chloro-4-fluorophenyl)bicyclo[3.1.1]heptane-3-carboxamide;
- 6,6-Dimethyl-2,4-dioxo-N-[4-fluoro-3-(trifluoromethyl)phenyl]bicyclo[3.1.1]heptane-3-carboxamid
- 6,6-Dimethyl-2,4-dioxo-N-(3,4-dichlorophenyl)bicyclo[3.1.1]heptane-3-carboxamide;
- 6,6-Dimethyl-2,4-dioxo-N-(3,5-dichlorophenyl)bicyclo[3.1.1]heptane-3-carboxamide;
- 6,6-Dimethyl-2,4-dioxo-N-(4-fluorophenyl)bicyclo[3.1.1]heptane-3-carboxamide;
- 6,6-Dimethyl-2,4-dioxo-N-(3-chlorophenyl)bicyclo[3.1.1]heptane-3-carboxamide;
- 6,6-Dimethyl-2,4-dioxo-N-(4-chlorophenyl)bicyclo[3.1.1]heptane-3-carboxamide; or
- N-[3,5-bis(trifluoromethyl)phenyl]-2,4-dioxobicyclo[3.2.2]nonane-3-carboxamide; or tautomers thereof, pharmaceutically acceptable salts thereof, or both.

22. A compound of claim 1 selected from the group consisting of:
- (1S)-N-[3,5-bis(trifluoromethyl)phenyl]-1,8,8-trimethyl-2,4-dioxobicyclo[3.2.1]octane-3-carboxamide;
- (1S)-N-[3-(trifluoromethyl)phenyl]-1,8,8-trimethyl-2,4-dioxobicyclo[3.2.1]octane-3-carboxamide;
- (1S)-N-(3,5-dichlorophenyl)-1,8,8-trimethyl-2,4-dioxobicyclo[3.2.1]octane-3-carboxamide;
- (1S)-N-(3,4-dichlorophenyl)-1,8,8-trimethyl-2,4-dioxobicyclo[3.2.1]octane-3-carboxamide;
- (1S)-N-(3-nitrophenyl)-1,8,8-trimethyl-2,4-dioxobicyclo[3.2.1]octane-3-carboxamide;
- (1S)-N-(4-nitrophenyl)-1,8,8-trimethyl-2,4-dioxobicyclo[3.2.1]octane-3-carboxamide;
- (1S)-N-[4-chloro-3-(trifluoromethyl)phenyl]-1,8,8-trimethyl-2,4-dioxobicyclo[3.2.1]octane-3-carboxamide;
- (1S)-N-[4-fluoro-3-(trifluoromethyl)phenyl]-1,8,8-trimethyl-2,4-dioxobicyclo[3.2.1]octane-3-carbox
- (1S)-N-[4-(trifluoromethyl)phenyl]-1,8,8-trimethyl-2,4-dioxobicyclo[3.2.1]octane-3-carboxamide;
- (1S)-N-[4-(dimethylamino)phenyl]-1,8,8-trimethyl-2,4-dioxobicyclo[3.2.1]octane-3-carboxamide;
- (1S)-N-[3-chloro-4-fluorophenyl]-1,8,8-trimethyl-2,4-dioxobicyclo[3.2.1]octane-3-carboxam
- (1S)-N-[4-chlorophenyl]-1,8,8-trimethyl-2,4-dioxobicyclo[3.2.1]octane-3-carboxamide;
- (1S)-N-[4-methylphenyl]-1,8,8-trimethyl-2,4-dioxobicyclo[3.2.1]octane-3-carboxamide;

(1R)-N-[3,5-bis(trifluoromethyl)phenyl]-1,8,8-trimethyl-2,4-dioxobicyclo[3.2.1]octane-3-carboxamide;
(1R)-N-(3,5-dichlorophenyl)-1,8,8-trimethyl-2,4-dioxobicyclo[3.2.1]octane-3-carboxamide;
(1R)-N-(3,4-dichlorophenyl)-1,8,8-trimethyl-2,4-dioxobicyclo[3.2.1]octane-3-carboxamide;
(1R)-N-(3-nitrophenyl)-1,8,8-trimethyl-2,4-dioxobicyclo[3.2.1]octane-3-carboxamide;
(1R)-N-(4-nitrophenyl)-1,8,8-trimethyl-2,4-dioxobicyclo[3.2.1]octane-3-carboxamide;
(1R)-N-[4-chloro-3-(trifluoromethyl)phenyl]-1,8,8-trimethyl-2,4-dioxobicyclo[3.2.1]octane-3-carboxamide;
(1R)-N-[3-(trifluoromethyl)phenyl]-1,8,8-trimethyl-2,4-dioxobicyclo[3.2.1]octane-3-carboxamide;
(1R)-N-[4-(trifluoromethyl)phenyl]-1,8,8-trimethyl-2,4-dioxobicyclo[3.2.1]octane-3-carboxamide;
(1R)-N-[4-chlorophenyl]-1,8,8-trimethyl-2,4-dioxobicyclo[3.2.1]octane-3-carboxamide;
(1R)-N-[3-chloro-4-fluorophenyl]-1,8,8-trimethyl-2,4-dioxobicyclo[3.2.1]octane-3-carboxamide; or
(1R)-N-[4-fluoro-3-(trifluoromethyl)phenyl]-1,8,8-trimethyl-2,4-dioxobicyclo[3.2.1]octane-3-carboxamide;
(1R)-N-[4-methylphenyl]-1,8,8-trimethyl-2,4-dioxobicyclo[3.2.1]octane-3-carboxamide; or
(1R)-N-[4-(dimethylamino)phenyl]-1,8,8-trimethyl-2,4-dioxobicyclo[3.2.1]octane-3-carboxamide; or
tautomers thereof, pharmaceutically acceptable salts thereof, or both.

23. A method for treating a mammal for neuronal hyperexcitability comprising administering to the mammal a therapeutically effective amount of at least one compound formula (I):

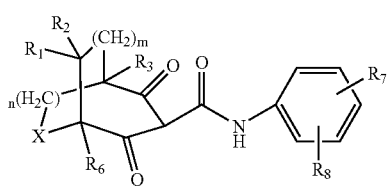

(I)

or a tautomer thereof, or a pharmaceutically acceptable salt thereof or both, wherein:
X is a bond or $CR_4R_5$;
$R_1$, $R_2$, $R_4$, and $R_5$ are, independently, hydrogen or a $C_1$ to $C_6$ alkyl;
$R_3$ and $R_6$ are, independently hydrogen or a $C_1$ to $C_6$ alkyl;
$R_7$ and $R_8$ are, independently, hydrogen, a halogen atom, a hydroxyl group, a $C_1$ to $C_6$ alkyl, a $C_1$ to $C_6$ alkoxy, a $C_1$ to $C_4$ perhalogenated alkyl, a $C_1$ to $C_4$ perhalogenated alkoxy, a $C_2$ to $C_7$ alkenyl, CN, $NO_2$, $CO_2R_9$, $COR_9$, alkanesulfonyl, or $NR_9R_{10}$;
m and n are, independently, 0 or 1; and
$R_9$ and $R_{10}$ are, independently, hydrogen or a $C_1$ to $C_6$ alkyl.

24. The method of claim 23 wherein the condition treated is selected from at least one of convulsions, epilepsy, episodic ataxia, myokymia, neonatal convulsions, cerebral ischemia, cerebral palsy, stroke, traumatic brain injury, traumatic spinal cord injury, asphyxia, anoxia or prolonged cardiac surgery.

25. A method of treating a condition selected from epilepsy, stroke, or anxiety disorder in a mammal comprising administering to the mammal a therapeutically effective amount of at least one compound formula (I):

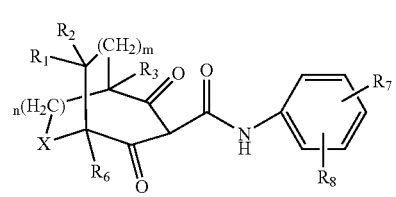

(I)

or a tautomer thereof, or a pharmaceutically acceptable salt thereof or both, wherein:
X is a bond or $CR_4R_5$;
$R_1$, $R_2$, $R_4$, and $R_5$ are, independently, hydrogen or a $C_1$ to $C_6$ alkyl;
$R_3$ and $R_6$ are, independently hydrogen or a $C_1$ to $C_6$ alkyl;
$R_7$ and $R_8$ are, independently, hydrogen, a halogen atom, a hydroxyl group, a $C_1$ to $C_6$ alkyl, a $C_1$ to $C_6$ alkoxy, a $C_1$ to $C_4$ perhalogenated alkyl, a $C_1$ to $C_4$ perhalogenated alkoxy, a $C_2$ to $C_7$ alkenyl, CN, $NO_2$, $CO_2R_9$, $COR_9$, alkanesulfonyl, or $NR_9R_{10}$;
m and n are, independently, 0 or 1; and
$R_9$ and $R_{10}$ are, independently, hydrogen or a $C_1$ to $C_6$ alkyl.

26. A pharmaceutical composition comprising:
a) a therapeutically effective amount of at least one compound of formula I, or a tautomer thereof, or a pharmaceutically acceptable salt thereof, or both:

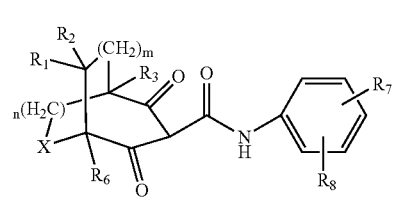

(I)

wherein:
X is a bond or $CR_4R_5$;
$R_1$, $R_2$, $R_4$, and $R_5$ are, independently, hydrogen or a $C_1$ to $C_6$ alkyl;
$R_3$ and $R_6$ are, independently hydrogen or a $C_1$ to $C_6$ alkyl;
$R_7$ and $R_8$ are, independently, hydrogen, a halogen atom, a hydroxyl group, a $C_1$ to $C_6$ alkyl, a $C_1$ to $C_6$ alkoxy, a $C_1$ to $C_4$ perhalogenated alkyl, a $C_1$ to $C_4$ perhalogenated alkoxy, a $C_2$ to $C_7$ alkenyl, CN, $NO_2$, $CO_2R_9$, $COR_9$, alkanesulfonyl, or $NR_9R_{10}$;
m and n are, independently, 0 or 1; and
$R_9$ and $R_{10}$ are, independently, hydrogen or a $C_1$ to $C_6$ alkyl; and
(b) at least one pharmaceutically acceptable carrier.

27. A process for preparing a bicyclo[3.1.1]heptane-2,4-dione comprising subjecting a compound of formula (IIa):
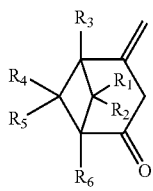
to ozonolysis to form a bicyclo[3.1.1]heptane-2,4-dione of formula III
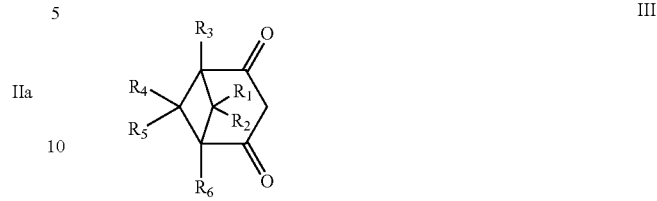
wherein:
$R_1$, $R_2$, $R_4$, and $R_5$ are, independently, hydrogen or a $C_1$ to $C_6$ alkyl; and
$R_3$ and $R_6$ are, independently hydrogen or a $C_1$ to $C_6$ alkyl.
* * * * *